(12) United States Patent
Ouchi

(10) Patent No.: US 6,395,003 B1
(45) Date of Patent: *May 28, 2002

(54) DRAINAGE TUBE INDWELLING DEVICE FOR ENDOSCOPE

(75) Inventor: Teruo Ouchi, Saitama-ken (JP)

(73) Assignee: Asahi Kogaku Kogyo Kabushiki Kaisha, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 21 days.

(21) Appl. No.: 09/390,994

(22) Filed: Sep. 7, 1999

(30) Foreign Application Priority Data

Sep. 8, 1998 (JP) .......................... 10-254256
Feb. 25, 1999 (JP) .......................... 11-047282

(51) Int. Cl.⁷ .............................................. A61B 18/18
(52) U.S. Cl. ........................ 606/46; 606/41; 604/264
(58) Field of Search ................. 606/41, 45, 46, 606/48–50; 604/21, 22, 164.01, 264, 272, 523

(56) References Cited

U.S. PATENT DOCUMENTS

| 3,595,239 A | * | 7/1971 | Petersen ........................ 606/45 |
| 4,500,313 A | | 2/1985 | Young |
| 4,973,305 A | | 11/1990 | Goltzer |
| 5,084,022 A | * | 1/1992 | Claude .......................... 604/164 |
| 5,114,401 A | | 5/1992 | Stuart et al. |
| 5,178,620 A | * | 1/1993 | Eggers et al. .................. 606/41 |
| 5,431,639 A | * | 7/1995 | Shaw ............................ 604/264 |
| 5,605,539 A | | 2/1997 | Buelna et al. |
| 5,693,030 A | | 12/1997 | Lee et al. |
| 5,876,400 A | * | 3/1999 | Songer ........................... 606/45 |
| 5,921,952 A | * | 7/1999 | Desmond, III et al. ......... 604/8 |
| 6,059,719 A | * | 5/2000 | Yamamoto et al. .......... 600/127 |
| 6,134,467 A | * | 10/2000 | Ouchi ............................ 604/21 |

FOREIGN PATENT DOCUMENTS

| DE | 19847852 | 4/1999 |
| EP | 0834288 | 4/1998 |
| FR | 767414 | 7/1934 |
| JP | 63-24883 | 7/1988 |
| JP | 2000-14769 | 1/2000 |
| WO | 99/43263 | 9/1999 |

* cited by examiner

Primary Examiner—Michael Peffley
(74) Attorney, Agent, or Firm—Greenblum & Bernstein P.L.C.

(57) ABSTRACT

A drainage tube indwelling device for an endoscope is provided with a drainage tube formed of insulating material, a guide wire formed of electrically conductive material, a connector that connects the guide wire with a high-frequency power source, and a fixing device capable of fixing the drainage tube with respect to the guide wire. The drainage tube is longer than a length of a treatment insertion channel of the endoscope, and the guide wire is longer than the drainage tube. The guide wire is slidably inserted in the drainage tube so that a distal end portion of the guide wire can be protruded from a distal end of the drainage tube.

20 Claims, 24 Drawing Sheets

DRAINAGE TUBE INDWELLING DEVICE FOR ENDOSCOPE

BACKGROUND OF THE INVENTION

The present invention relates to a drainage tube indwelling device for indwelling a drainage tube, which is used to drain secreted liquid remaining inside a human body to outside the human body, in the human body it has been known that, when a bile duct is narrowed or clogged, bile secreted from the deep recess thereof may not be drained, and jaundice is caused. In such a case, a distal end of a relatively long drainage tube is inserted in Vater's papilla, which is an end portion of a bile duct toward a duodenum using an endoscope, and indwell the drainage tube with the proximal end of the drainage tube located outside the body of the patient through the nose.

If the Vater's papilla is suffered from cancer or the like, the drainage tube may not be inserted therein since the tissue is hardened or deformed. Thus, in such a case, the jaundice cannot be endoscopically treated to lighten the same.

SUMMARY OF THE INVENTION

It is therefore an object of the invention to provide an improved drainage tube indwelling device which enables indwelling of the drainage tube regardless of the condition of the narrowed portion.

For the above object, according to the present invention, there is provided a drainage tube indwelling device for an endoscope, which is provided with: a drainage tube formed of electrically insulating flexible material, the drainage tube being longer than a length of a treatment insertion channel of the endoscope, the drainage tube being slidably inserted in the treatment insertion channel;

a guide wire formed of electrically conductive material, the guide wire being longer than the drainage tube, the guide wire being slidably inserted in the drainage tube, a distal end portion of the guide wire being able to protrude from a distal end of the drainage tube;

a connector that connects the guide wire with a high-frequency power source; and a fixing device capable of fixing the drainage tube with respect to the guide wire.

Firstly, the drainage tube is located at a target position with the guide wire inserted therein. Then, the guide wire, which is protruded from a drainage tube, is energized with a high-frequency current to transfix the target position (i.e., the inner wall of the human cavity). Then, the drainage tube is indwelled such that the tip end thereof is located at the deep recess of the transfixed portion. Therefore, regardless of the narrowed portion, the secreted liquid can be drained outside, and an excellent treatment effect can be obtained.

Optionally, the connector and the fixing device are integrally formed and provided at a proximal end of the drainage tube.

Further optionally, the drainage tube indwelling device may be provided with an electrically insulating flexible tube provided between the proximal end portion of the drainage tube to a proximal end of the guide wire. By the flexible tube, a portion of the guide wire located between the proximal end of the drainage tube and the proximal end of the guide wire is prevented from being exposed to outside. The fixing device may be constituted to fix/release the drainage tube, the guide wire and the flexible tube with each other.

Alternatively, the fixing device may be constituted to fix/release only the drainage tube and the guide wire. In this case, an operation unit may be provided for moving the fixing device in an axial direction of the drainage tube.

In particular, the operation unit may include a stationary unit to be secured at an inlet of the insertion channel of the endoscope, and a slider unit which is slidable with respect to the stationary unit and drives the fixing device to move in the axial direction.

Still optionally, an indicating system may be provided for indicating a positional relationship between the drainage tube and the guide wire in an axial direction thereof.

If the distal end of the guide wire is formed to be sharp-pointed, the insertion channel may be broken when the guide wire proceeds inside the insertion channel. In order to avoid such a problem, there is provided a drainage tube indwelling device for an endoscope, provided with:

a drainage tube;

a guide wire that is to be inserted in the drainage tube, the drainage tube being inserted in an accessory insertion channel of the endoscope with the guide wire inserted;

an adjustment member for adjusting a positional relationship between the drainage tube and the guide wire in an axial direction; and an indicating system for indicating a positional relationship between the drainage tube and the guide wire in the axial direction.

Since the protruded amount of the distal end portion of the guide wire can be adjusted, the protruded/retracted amount of the distal end portion can be recognized. Therefore, when the drainage tube indwelling device is inserted in a treatment accessory insertion channel of the endoscope, retraction of the end portion of the guide wire can be confirmed, and the insertion channel may not be damaged by the tip of the end portion even if it is sharp-pointed.

Optionally, the indicating system includes an indication mark provided on the guide wire. Alternatively or optionally, the indication mark may be provided on the drainage tube.

Further optionally, the drainage tube indwelling device may be provided with a transparent tube member on a proximal end side of the adjusting mechanism. The transparent tube functions to cover the proximal end portion of the guide wire, and further a positional relationship between the drainage tube and the guide wire is observable since the proximal ends of the guide wire and the drainage tube can be observed through the transparent tube.

In this case, the indication mark can be provided on the transparent tube.

Optionally, a pusher tube may be provided on the proximal end side of the drainage tube. The pusher tube may be fitted on the guide wire, and the distal end thereof may contact the proximal end of the drainage tube. The adjustment mechanism may adjust the positional relationship of the pusher tube with respect to the guide wire. In such a constitution, the indication mark may be provided on the guide wire, transparent tube, or pusher tube.

DESCRIPTION OF THE ACCOMPANYING DRAWINGS

DESCRIPTION OF THE EMBODIMENTS

The present invention will be described with reference to the accompanying drawings.

Figure 1:
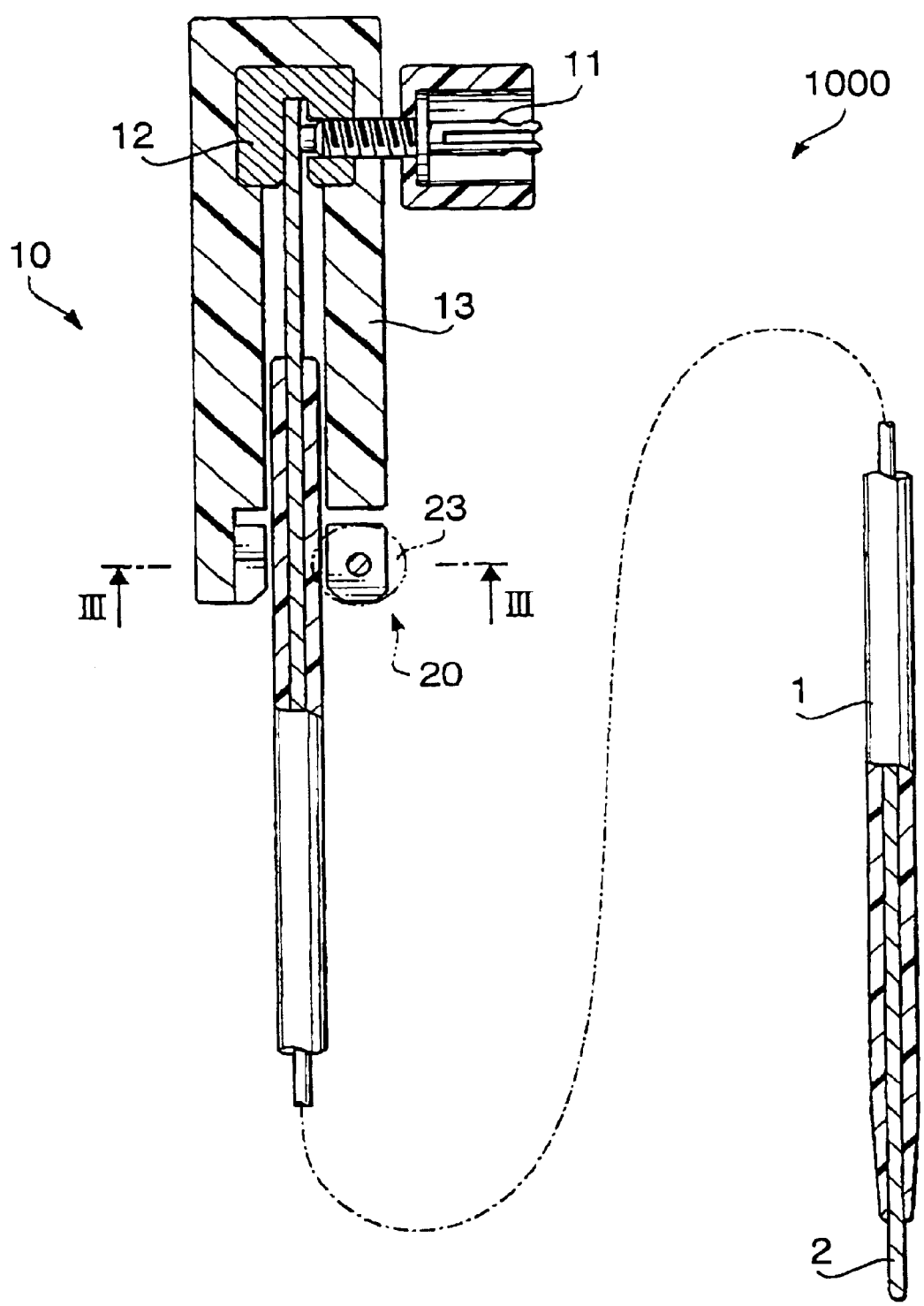
FIG. 1 shows a cross sectional view of a drainage tube indwelling device for an endoscope according to a first embodiment of the invention.

FIG. 1 shows a cross sectional view of a drainage tube indwelling device 1000 for an endoscope according to a first embodiment of the invention.

In FIG. 1, a reference numeral 1 denotes a drainage tube which is to be inserted in a treatment insertion channel of an endoscope, and then indwelled in the human body for draining the secreted liquid remaining in a narrowed portion inside the body to outside.

The drainage tube 1 is formed of a flexible tube having electrically insulating property. The drainage tube 1 is formed to be longer than a length of a channel of an endoscope used for indwelling. For example, the length of the drainage tube 1 may be 2 meters when the length of the channel of the endoscope is 1 meter.

Figure 2:
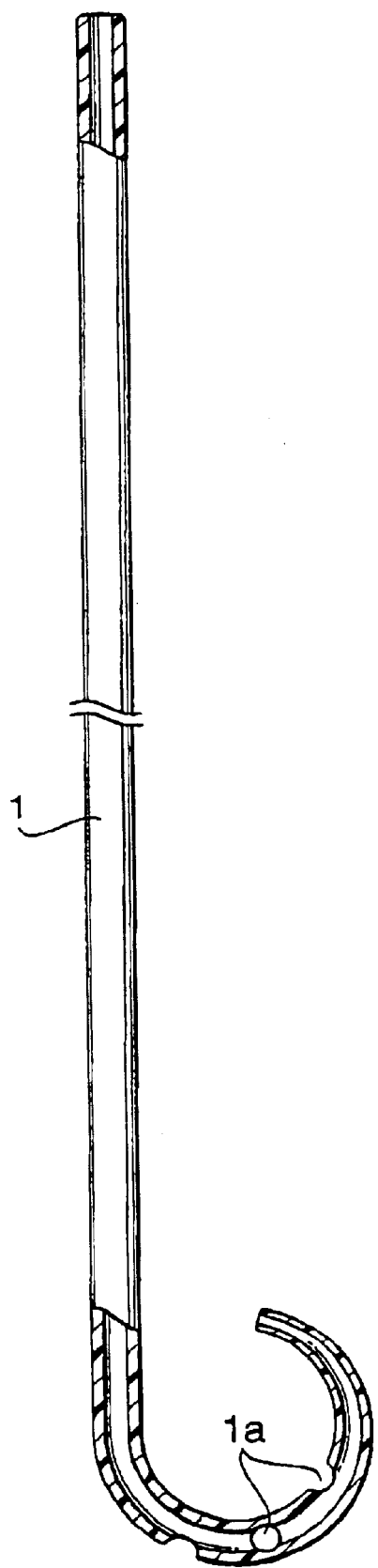
FIG. 2 shows an example of a drainage tube.

As shown in FIG. 2, a distal end portion of the drainage tube 1 is formed to have a smaller diameter towards the tip thereof. On the circumferential surface of the distal end portion of the drainage tube 1, a plurality of holes 1a are formed. The distal end portion of the drainage tube 1 is formed to curl in its neutral condition.

Inside the drainage tube 1, a flexible and electrically conductive guide wire 2 is slidably inserted (see FIG. 1). The guide wire 2 is formed to be longer than the drainage tube 1. When the proximal end portion of the guide wire 2 is protruded from the proximal end of the drainage tube, the tip of the guide wire 1 is protruded from the distal end of the drainage tube 1.

To the distal end of the drainage tube 1, a connector unit 10 is connected. The connector unit 10 is provided with a connector 11 which is to be connected with a power cord of a high-frequency power source (not shown).

The connector unit 10 is constituted such that a root portion of the connector 11 is screwed in a conductive block 12 which is built in a electrically insulating housing 13. The proximal end of the guide wire 2 is press-secured onto the conductive block 12 by the screwed connector 11. With this constitution, by connecting the high-frequency power cord to the connector 11, the guide wire 2 can by energized with a high-frequency current.

The connector unit 10 is provided with a fixing device 20 which is used for fixing or unfixing the drainage tube 1 with respect to the guide wire 2.

Figure 3:
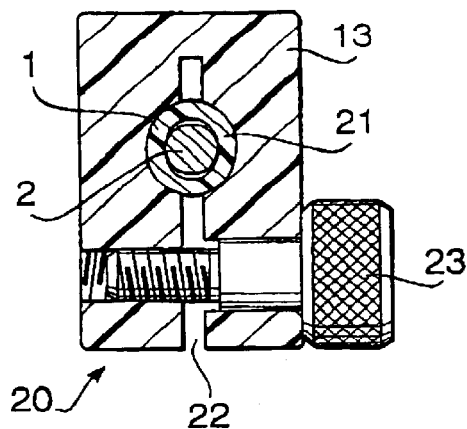
FIG. 3 shows a cross sectional view of the fixing device taken on the line III—III of FIG. 1.

FIG. 3 shows a cross sectional view of the fixing device 20 taken on the line III—III of FIG. 1. The fixing device 20 is substantially a rectangular solid, and formed with an insertion hole 21, through which the drainage tube 1 is slidably inserted. Further, a slit 22 passing the insertion hole 21 is formed, and a screw 23 for narrowing the slit 22 is provided.

When the screw 23 is fastened tightly, as shown in FIG. 3, the drainage tube 1 is pressed from both side walls, and press-contacts the guide wire 2. Therefore, drainage tube 1 is fixed onto the guide wire 2.

When the screw 23 is loosened, the drainage tube 1 is allowed to slide with respect to the guide wire 2, and therefore, the drainage tube 1 can be removed from the housing 13. By loosening the connecting terminal 11, the guide wire 2 can also be removed from the housing 13.

Figure 4:
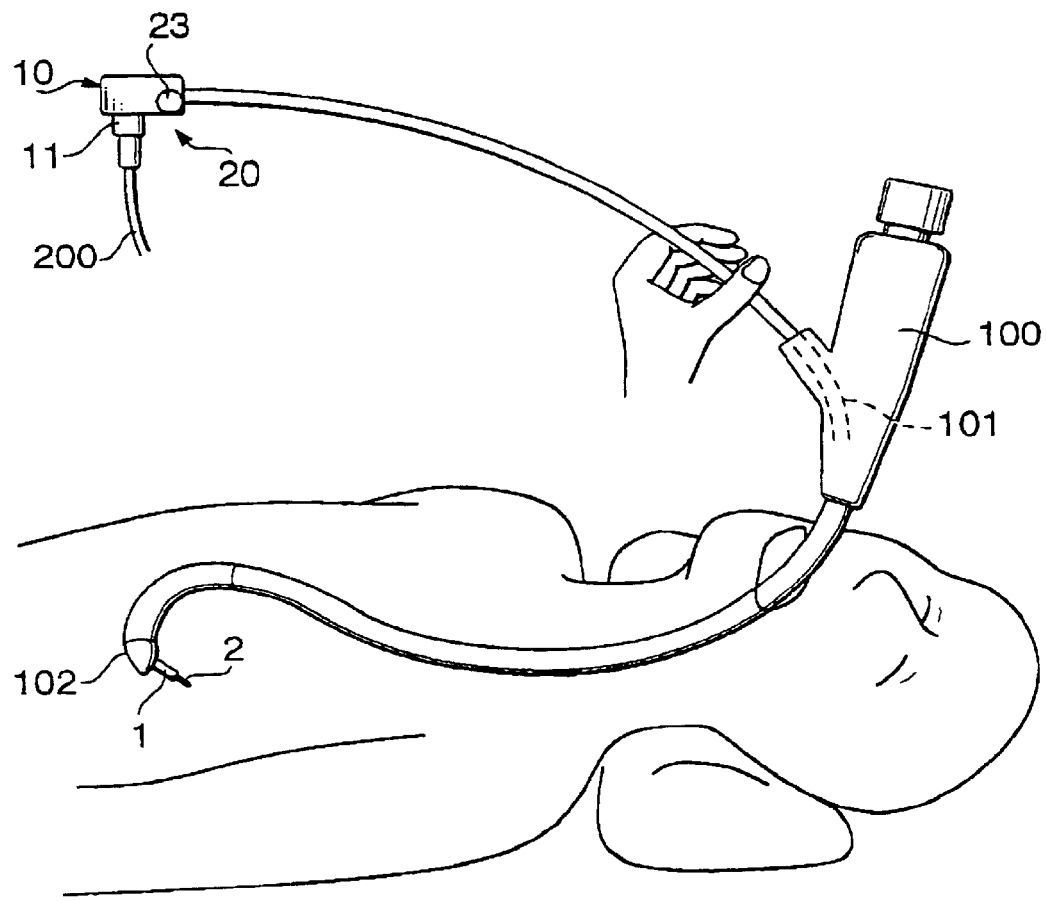
FIGS. 4–6 show usage of thus constructed drainage tube indwelling device according to the first embodiment.
Figure 5:
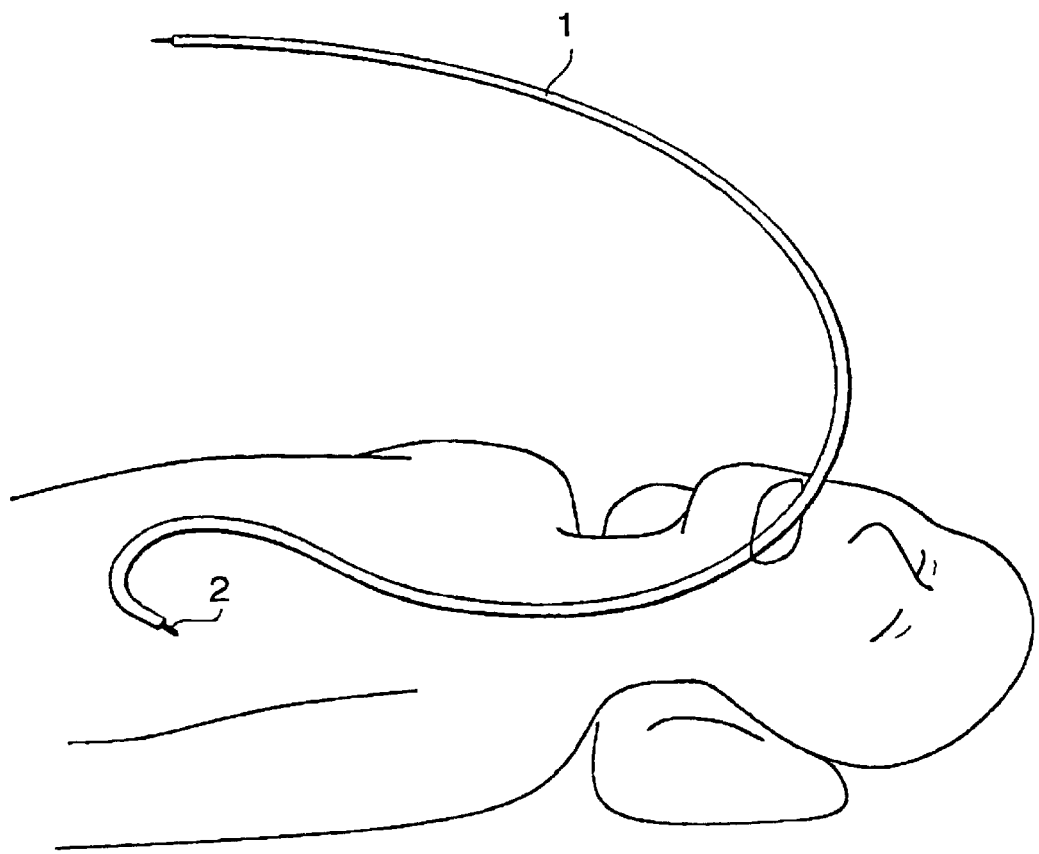
Figure 6:
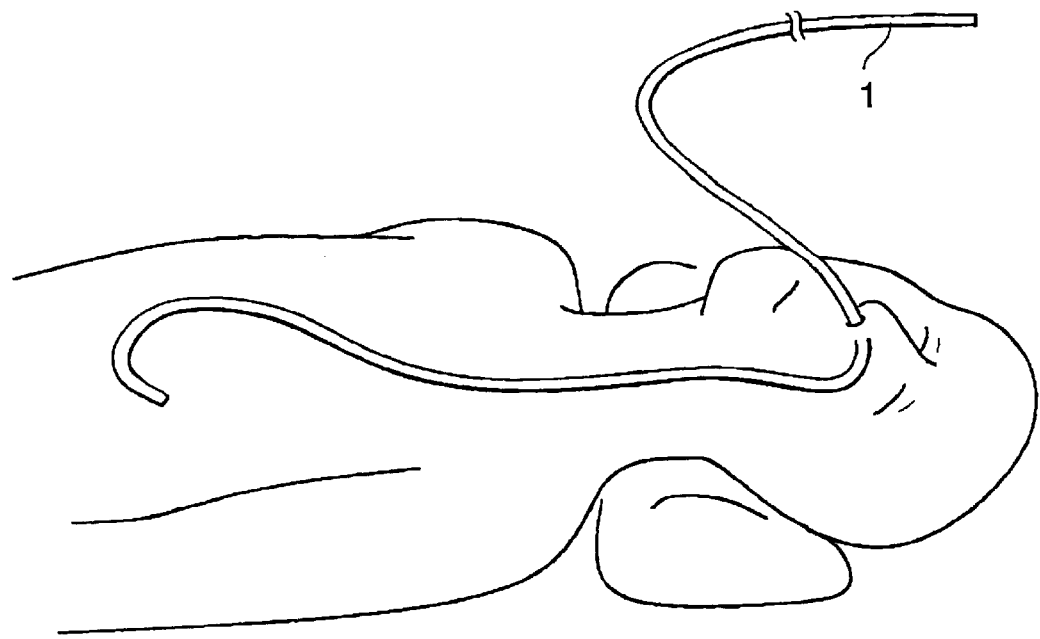

FIGS. 4–6 show usage of thus constructed drainage tube indwelling device according to the first embodiment.

When the drainage tube 1 is to be indwelled, firstly, the tip of the guide wire 2 is made protruded from the distal end of the drainage tube 1 by a certain amount, and the fixing device 20 is operated (i.e., the screw 23 is fastened) to fix the drainage tube 1 with respect to the guide wire.

In this condition, if the drainage tube 1 is pushed forward at the proximal end of an endoscope 100 and press the distal end of the guide wire 2 against something hard, the tip end of the guide wire 2 may be pushed inside the drainage tube 1 in some degree. It may be preferable that the positional relationship between the guide wire 2 and the drainage tube 1 is adjusted such that the guide wire 2 protrudes by approximately 5 millimeters in the above condition (i.e., when the tip of the guide wire 2 is pushed to inside of the drainage tube).

The connector 11 should be connected with a high-frequency power cord 200.

The drainage tube indwelling device is then inserted in a treatment accessory insertion channel 101 of the endoscope 100 as shown in FIG. 4 and causes the tip portion to protrude from the distal end 102 of the endoscope 100.

Then, the tip of the drainage tube indwelling device is located inside a stomach, duodenum or the like, the tip of the guide wire 2 is pressed against the wall thereof, directed toward the bile duct, pancreatic duct or the like, and then the guide wire 2 is energized with the high-frequency current.

As the guide wire 2 is energized, the wall of the stomach, duodenum or the like is cauterized and a hole is formed to the bile duct, pancreatic duct or the like. Then, by loosening the screw 23 of the fixing device 20 for allowing the drainage tube 1 to move, and then the distal end of the drainage tube 1 is inserted, with being guided by the guide wire 2, toward the bile duct, pancreatic duct or the like.

Then, the connector 11 is loosened and the connector unit 10 is removed from the proximal end portions of the drainage tube 1 and the guide wire 2. Further, the endoscope 100 is removed with remaining the drainage tube 1 and the guide wire 2 as shown in FIG. 5.

Next, the guide wire 2 is withdrawn from the drainage tube 1, and the distal end portion of the drainage tube, which was extruded from the mouth is extruded from the nose as shown in FIG. 6.

In this state, the secreted liquid such as bile or pancreatic juice is drained through the drainage tube 1.

Figure 7A:
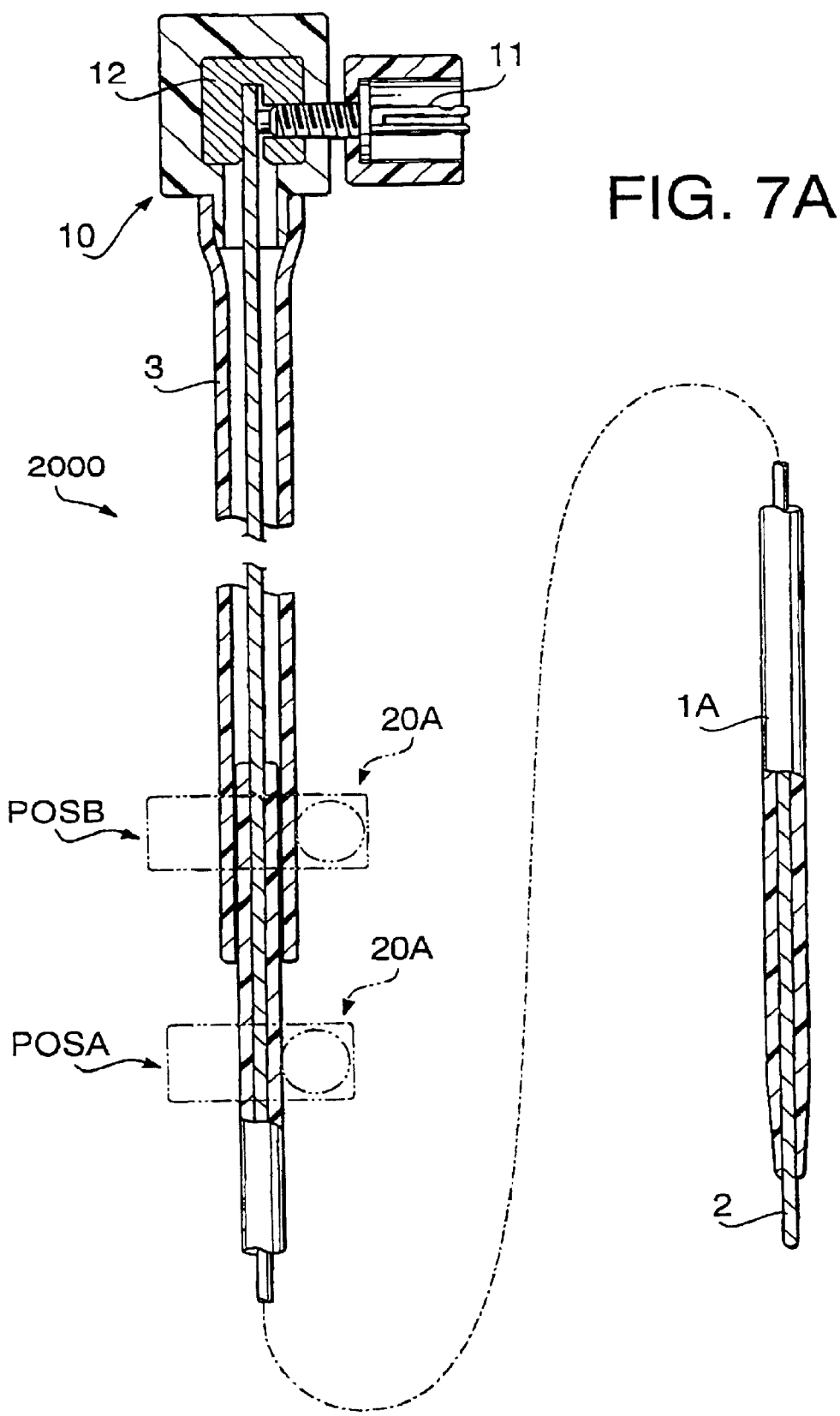
FIG. 7A shows a cross section of a drainage tube indwelling device according to a second embodiment.

FIG. 7A shows a cross section of a drainage tube indwelling device 2000 according to a second embodiment of the invention.

In the second embodiment, the connector unit 10 and the fixing device 20A are separated, and a flexible electrically-insulating cover tube 3 is provided between the drainage tube 1 and the connector unit 10 so that the guide wire 2 located between the proximal end of the drainage tube and the connector unit 10 is prevented from being exposed to outside.

With this construction, a movable range of the guide wire 2 with respect to the drainage tube 1 can be made sufficiently long.

The fixing device 20A may be located at position POSA where only the drainage tube 1 is fixed with respect to the guide wire 2, or at position POSB where the fixing device integrally fixes the cover tube 3, the drainage tube 1 and the guide wire 2.

Figure 7B:
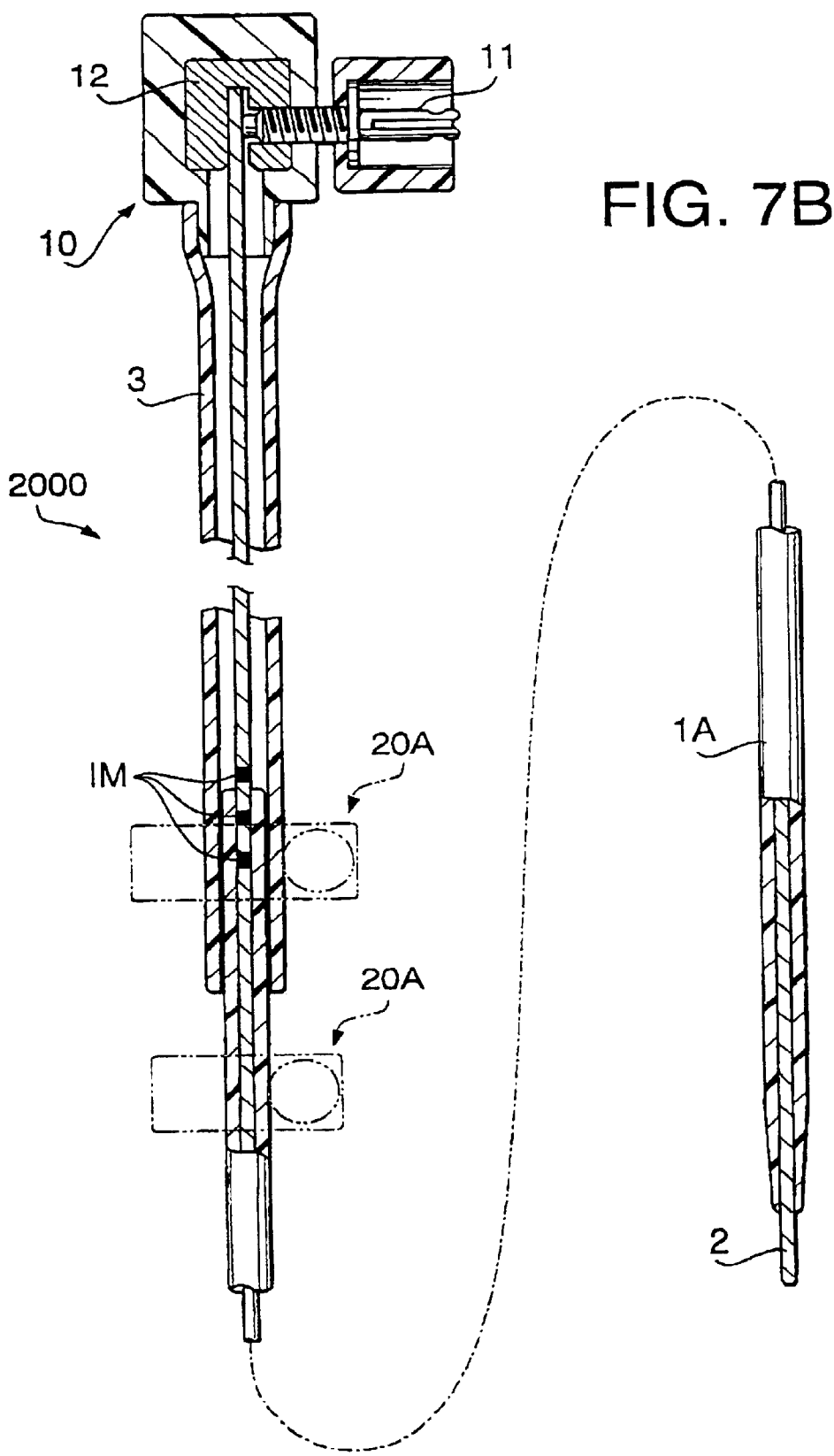
FIGS. 7B, 7C and 7D show modifications of the second embodiment.

FIG. 7B shows a modification of the second embodiment. In this modification, the cover tube 3 is made of transparent material so that the distal end of the drainage tube 2 and the guide wire 2 are observable from outside. Further, on the guide wire 2, indication marks IM are provided to indicate the protruded or retracted status/amount of the distal end of the guide wire with respect to the distal end of the drainage tube. By adjusting the position of the proximal end of the drainage tube 1 with respect to the marks IM on the guide wire 2, the protruded amount of the guide wire 2 with respect to the distal end of the drainage tube 1 can be adjusted.

Figure 7C:
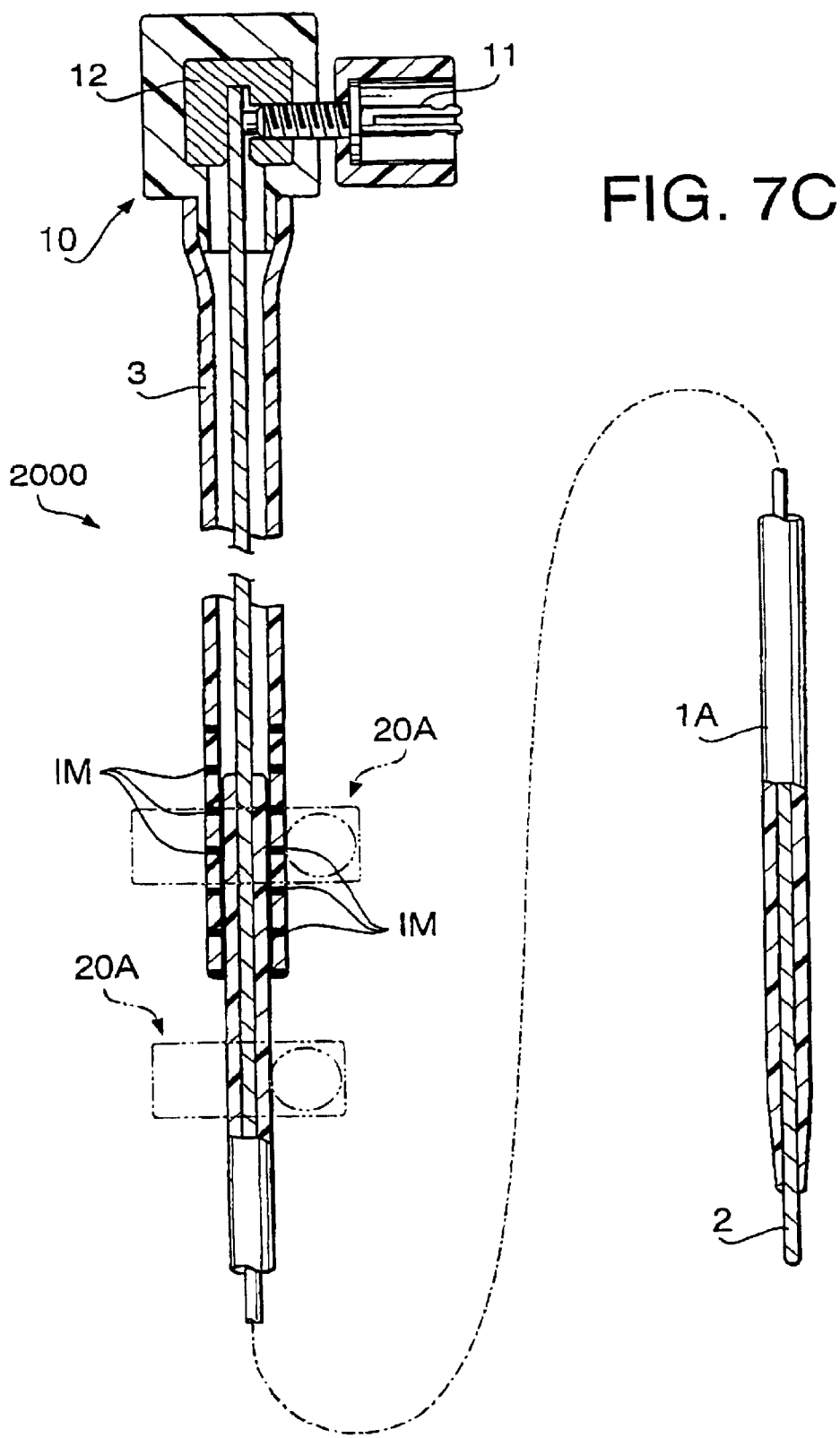

FIG. 7C shows another modification of the second embodiment. Also in this modification, the cover tube 3 is made of transparent material so that the distal end of the drainage tube 2 and the guide wire 2 are observable from outside. Further, on the cover tube 3, indication marks IM are provided to indicate a positional relationship between the drainage tube 1 with respect to the guide wire 2. By adjusting the position of the proximal end of the drainage tube 1 with respect to the marks IM of the cover tube 3, the protruded amount of the guide wire 2 with respect to the drainage tube 1 can be adjusted.

Figure 7D:
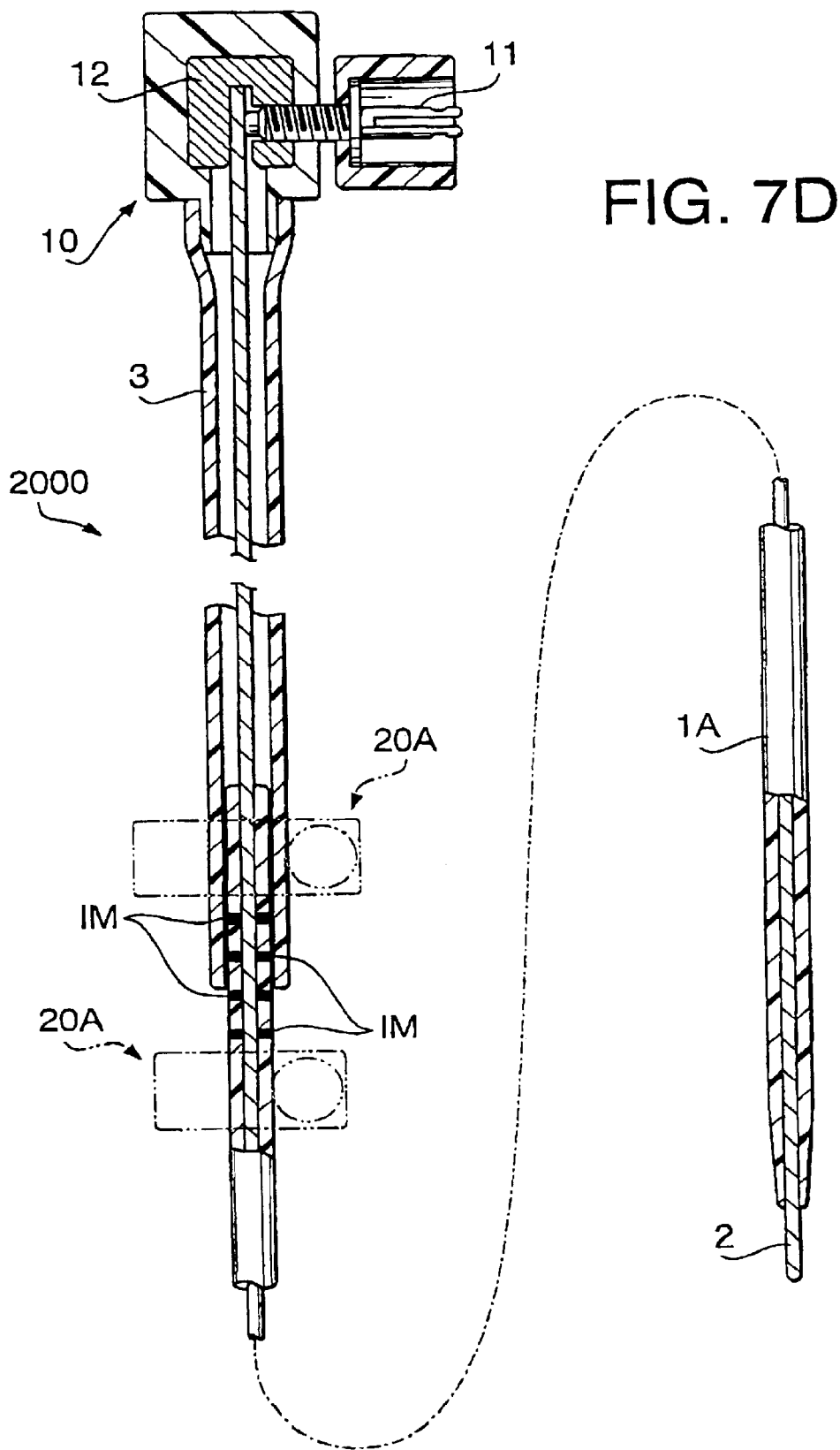

FIG. 7D shows a further modification of the second embodiment. In this modification, the cover tube 3 may not be made of transparent material. On the drainage tube 1, at a portion located adjacent to the distal end of the cover tube 3, indication marks IM are provided to indicate a positional relationship between the drainage tube 1 with respect to the cover tube 3. By adjusting the position of the drainage tube 1 with respect to the distal end side of the cover tube 3, the protruded amount of the guide wire 2 with respect to the drainage tube 1 can be adjusted.

Figure 8A:
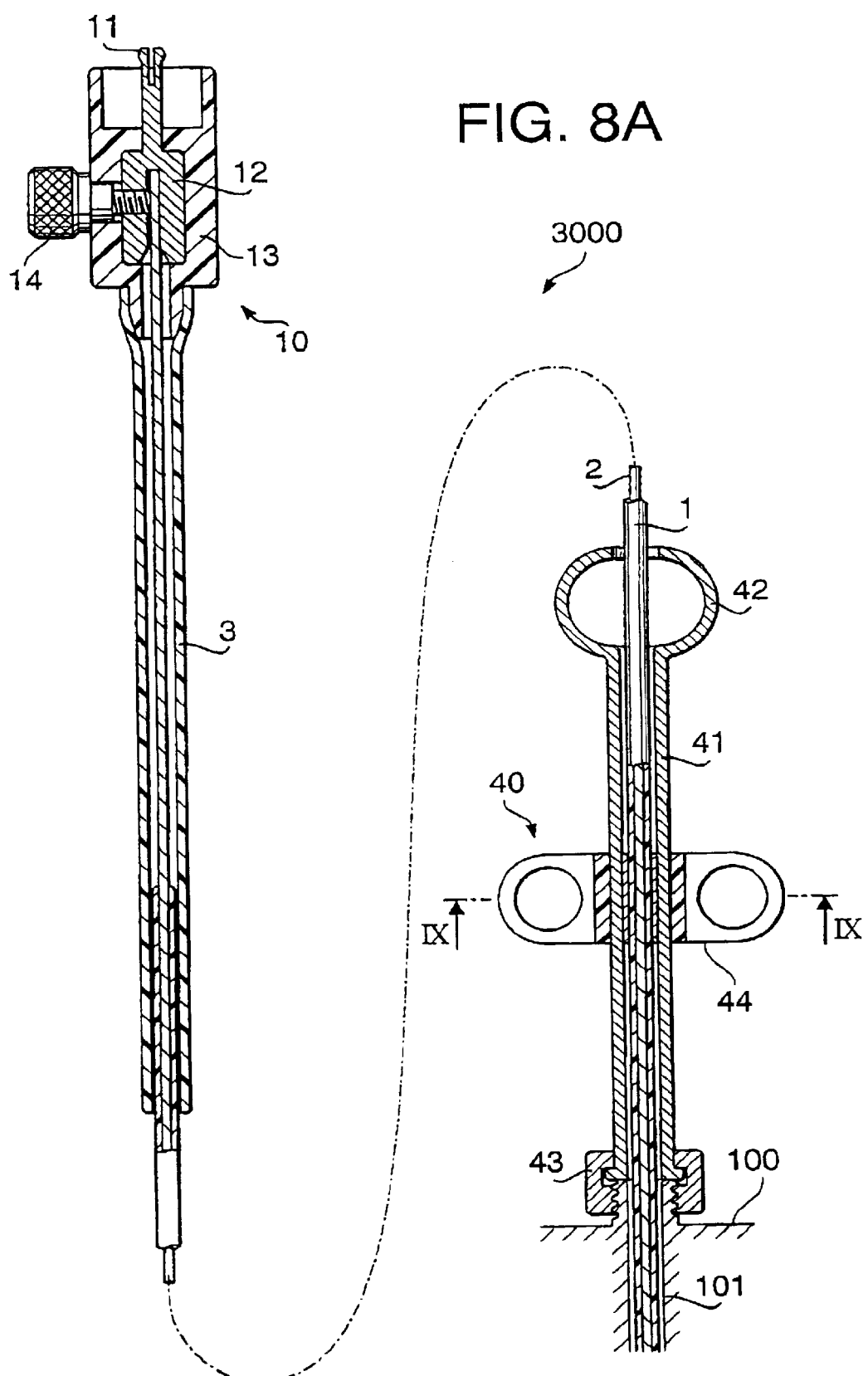
FIG. 8A shows a drainage indwelling device according to a third embodiment.

FIG. 8A shows a drainage indwelling device 3000 according to a third embodiment of the invention.

In the third embodiment, the fixing unit 20 employed in the first embodiment is not provided. Similar to the second embodiment, a flexible electrically-insulating cover tube 3 is provided between the proximal end portion of the drainage tube 1 and the connector unit 10 so that the guide wire 2 located between the proximal end of the drainage tube 1 and the connector unit 10 is prevented from being exposed to outside. In the third embodiment, the connector terminal 11 is protruded backward, along the axis of the guide wire 2, and therefore, the power cord is connected along the axis of the guide wire 2. A screw 14 for fixing the proximal end of the guide wire 2 to the connector unit 10 is provided separately from the connector terminal 11.

In the third embodiment, an operation unit 40, is detachably coupled to an inlet portion of the insertion channel 101 of an endoscope 100.

As shown in FIG. 8A, the operation unit 40 is elongated tubular body 41, and on the proximal side end of the body 41, a first hook 42 for a thumb is formed. On the other side end of the body 41, a connecting nut 43 is provided. The nut 43 is detachably engaged with the inlet of the insertion channel 101 in accordance with the Luer-Lok system.

A slider 44 is fitted around the body 41. The slider 44 is slidable along the axis of the guide wire 2. A pair of second hooks for forefinger and middle finger are provided to the slider 44.

Figure 9:
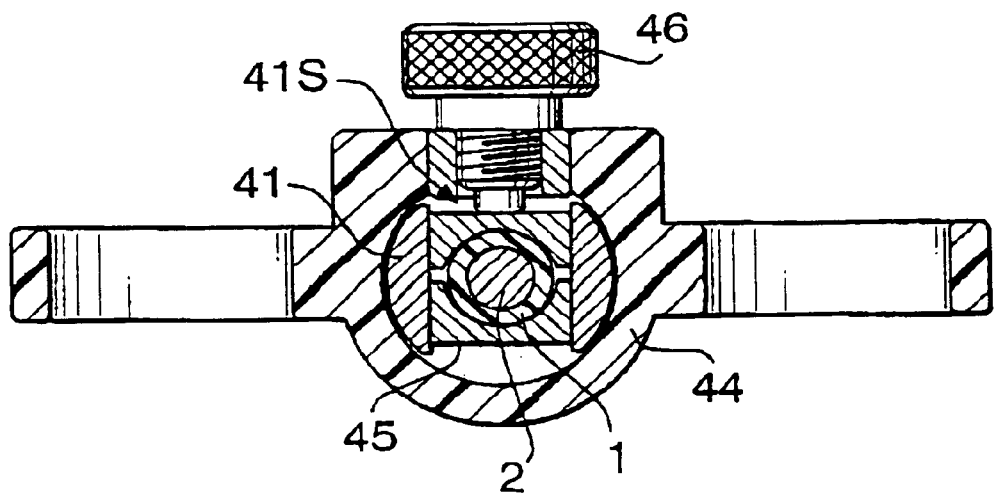
FIG. 9 is a cross sectional view of the slider taken along the line IX—IX of FIG. 8A.
Figure 10:
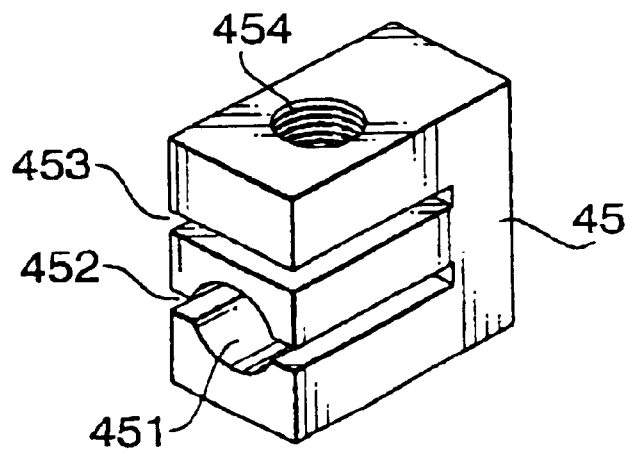
FIG. 10 shows a perspective view of a fixing block.

FIG. 9 is a cross section view of the slider 44 taken along the line IX—IX of FIG. 8A. The body 41 is formed with ia slit 41S extending along the axis of the guide wire 2, and a fixing block 45 as shown in FIG. 10 is loose fitted. The fixing block 45 is formed with a through hole 451 through which the drainage tube 1 is inserted. Further, a first slit 452 passing the center of the through hole 451, and a second slit 453 parallel to the first slit 452 are formed. A screw hole 454 is formed perpendicular to the slits 452 and 453.

A screw 46 is engaged with the screw hole 454, and the tip of the screw 46 abuts a portion between the slits 452 and 453. When the screw 46 is fastened, the fixing block 45 is deformed by the screw 46, and the drainage tube 1 and the guide wire 2 are fixed to each other. Thus, the drainage tube 1 and the guide wire 2 move integrally with the slider 44. If the screw 46 is loosened, the drainage tube 1 is movable with respect to the guide wire 2, and the slider 44 moves freely.

Figure 11:
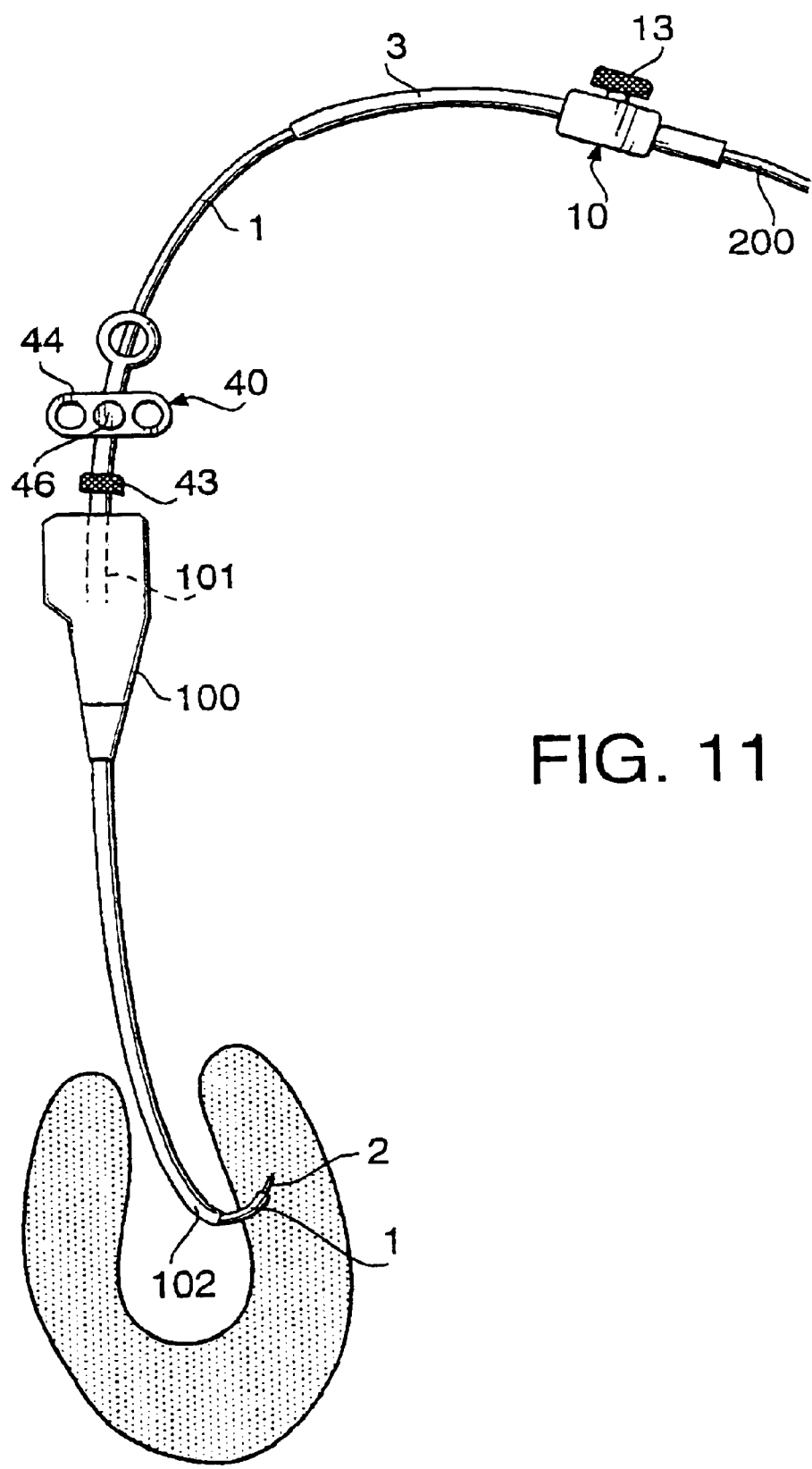
FIG. 11 shows usage of the drainage indwelling device according to the third embodiment.

FIG. 11 shows usage of the drainage indwelling device 3000 according to the third embodiment.

The drainage indwelling device 300 is connected to the endoscope with the connection nut 43. By sliding the slider 44 with the screw 46 fastened, a protruded amount of the drainage tube 1 and the guide wire 2 with respect to the distal end 102 of the insertion channel 101 of the endoscope 100 can be adjusted. Operation thereafter, i.e., the operation for indwelling the drainage tube 1 is similar to the operation in the first embodiment.

Figure 8B:
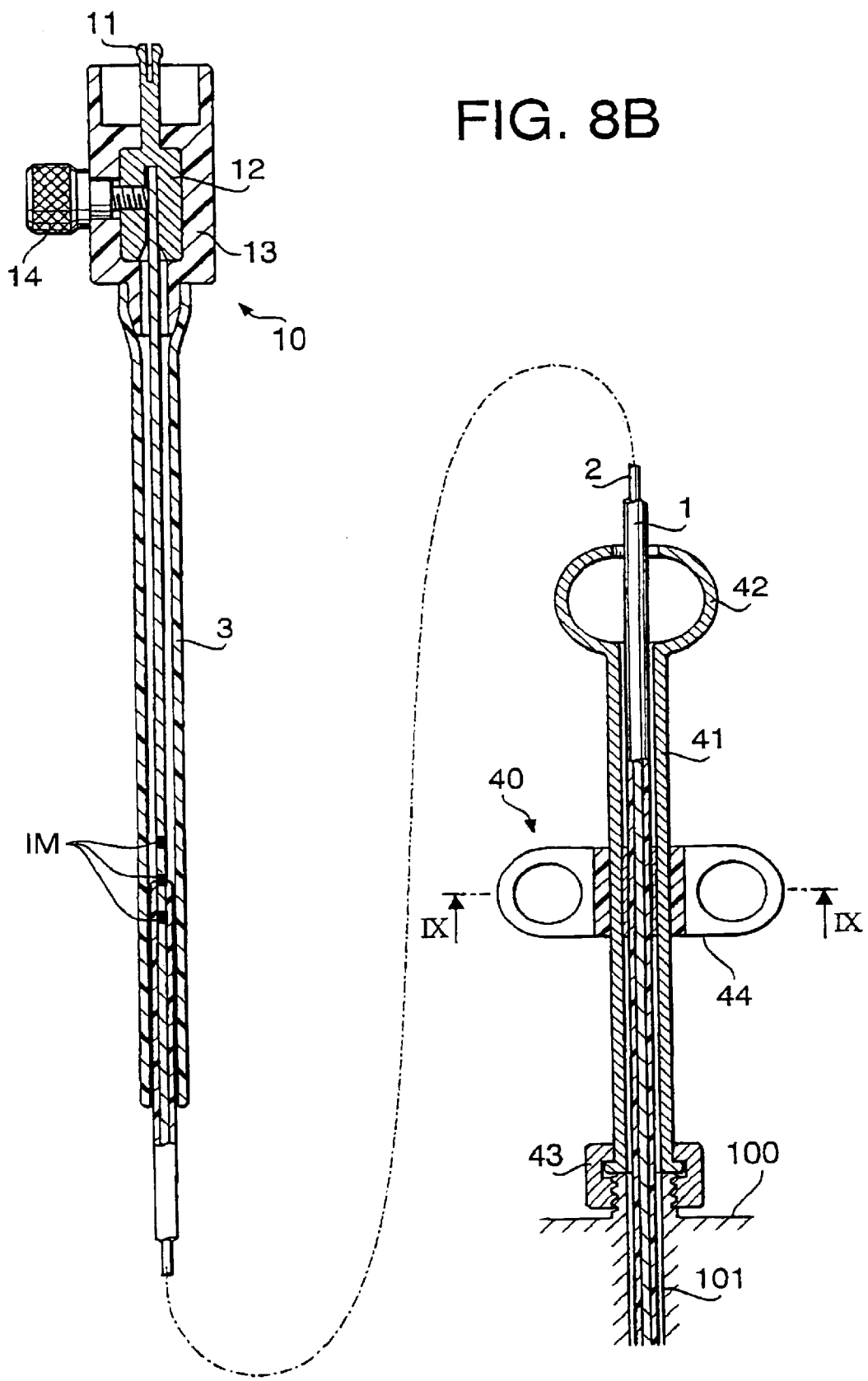
FIGS. 8B, 8C and 8D show modifications of the third embodiment.

FIG. 8B shows a modification of the third embodiment. In this modification, the cover tube 3 is made of transparent material similarly to the modification of the second embodiment so that the distal end of the drainage tube 1 and the guide wire 2 are observable from outside Further, on the guide wire 2, indication marks IM are provided to indicate the protruded or retracted status/amount of the distal end of the guide wire with respect to the distal end of the drainage tube. By adjusting the position of the proximal end of the drainage tube 1 with respect to the marks IM on the guide wire 2, the protruded amount of the guide wire 2 with respect to the distal end of the drainage tube 1 can be adjusted.

Figure 8C:
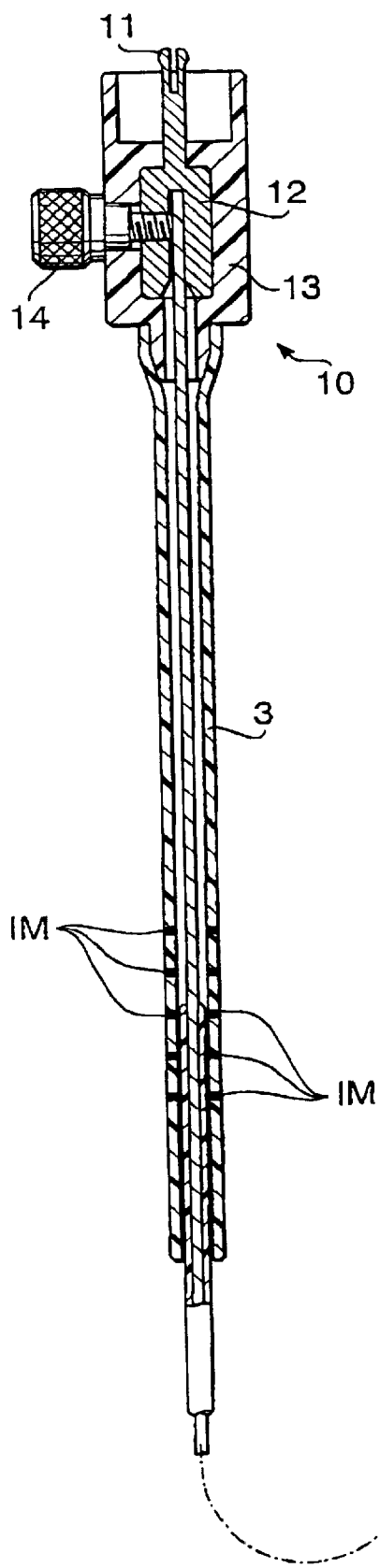
Figure 8C:
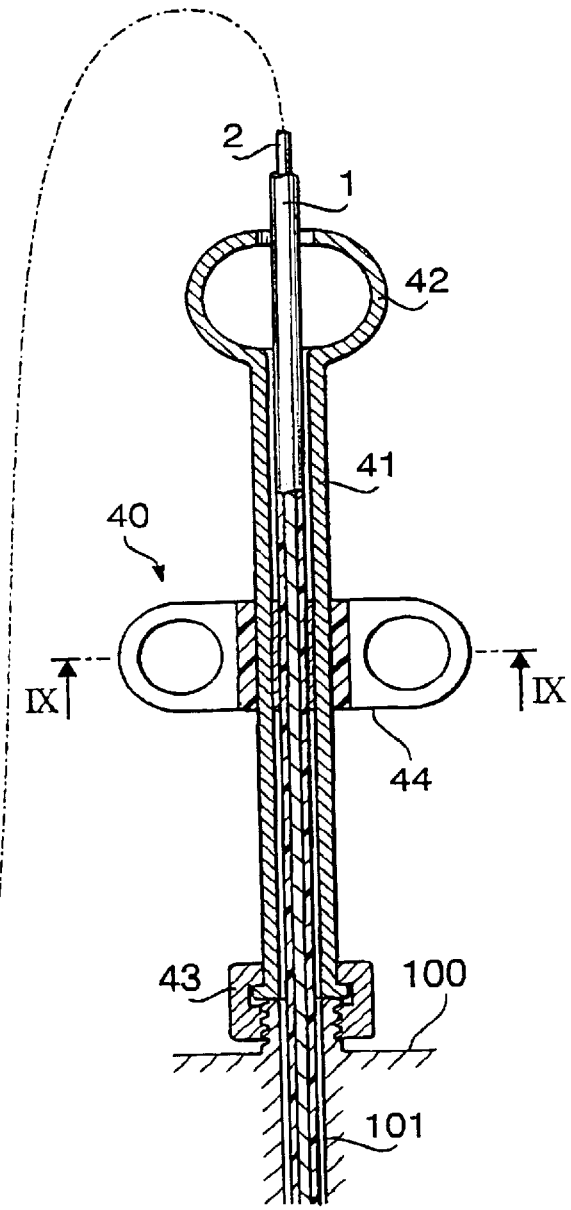

FIG. 8C shows another modification of the third embodiment. Also in this modification, the cover tube 3 is made of transparent material so that the distal end of the drainage tube 1 and the guide wire 2 are observable from outside. Further, on the cover tube 3, indication marks IM are provided to indicate a positional relationship between the drainage tube 1 with respect to the guide wire 2. By adjusting the position of the proximal end of the drainage tube 1 with respect to the marks IM of the cover tube 3, the protruded amount of the guide wire 2 with respect to the drainage tube 1 can be adjusted.

Figure 8D:
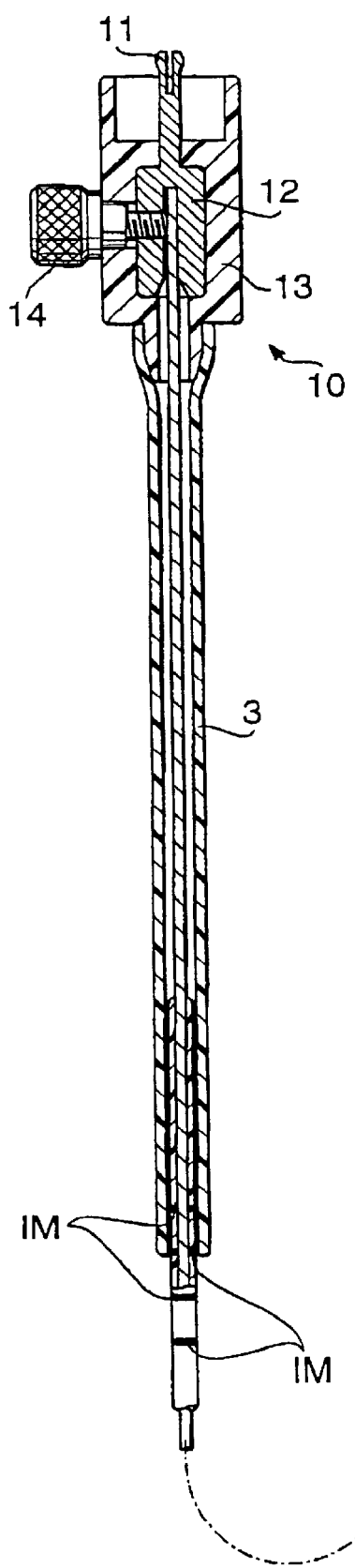
Figure 8D:
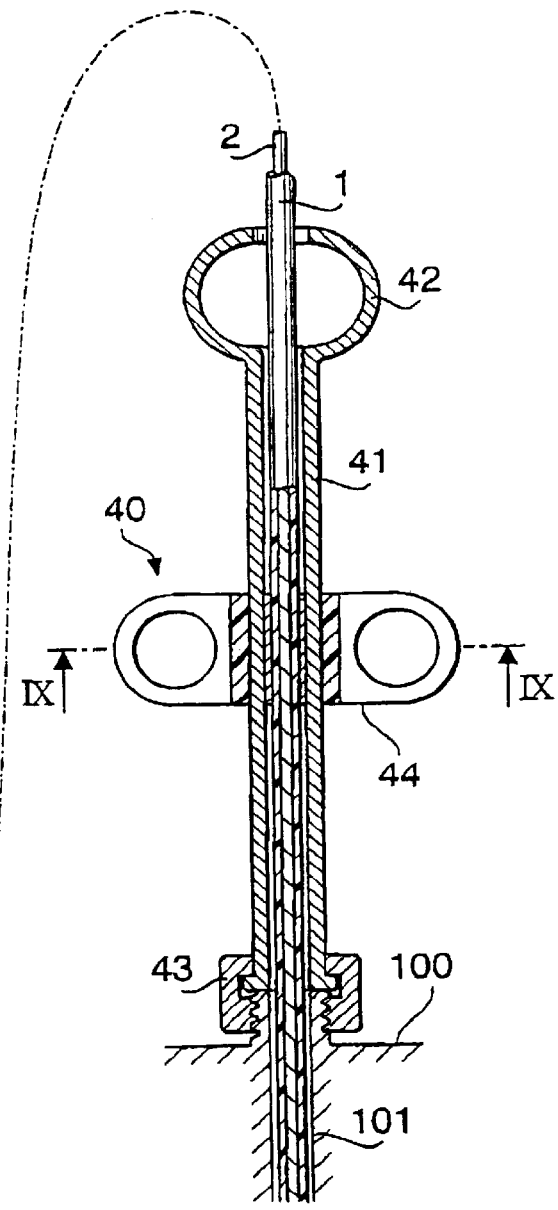

FIG. 8D shows a further modification of the third embodiment. In this modification, the cover tube 3 may not be made of transparent material. On the drainage tube 1, at a portion located adjacent to the distal end of the cover tube 3, indication marks IM are provided to indicate a positional relationship between the drainage tube 1 with respect to the cover tube 3. By adjusting the position of the drainage tube 1 with respect to the distal end side of the cover tube 3, the protruded amount of the guide wire 2 with respect to the drainage tube 1 can be adjusted.

As described above, according to the first through third embodiments and modifications thereof, a guide wire, which is protruded from a drainage tube, is energized with a high-frequency current to transfix the inner wall of the human cavity, and the drainage tube can be indwelled such that the tip end thereof is located at the deep recess of the transfixed portion. Therefore, regardless of the narrowed portion, the secreted liquid can be drained outside, and an excellent treatment effect can be obtained.

If the distal end portion 2a of the guide wire is sharp-pointed, the insertion channel of the endoscope may be broken by the sharp-pointed tip end of the guide wire when it is inserted through the insertion channel. Hereinafter, improvement of the drainage tube indwelling device avoiding such a problem will be described.

Figure 12A:
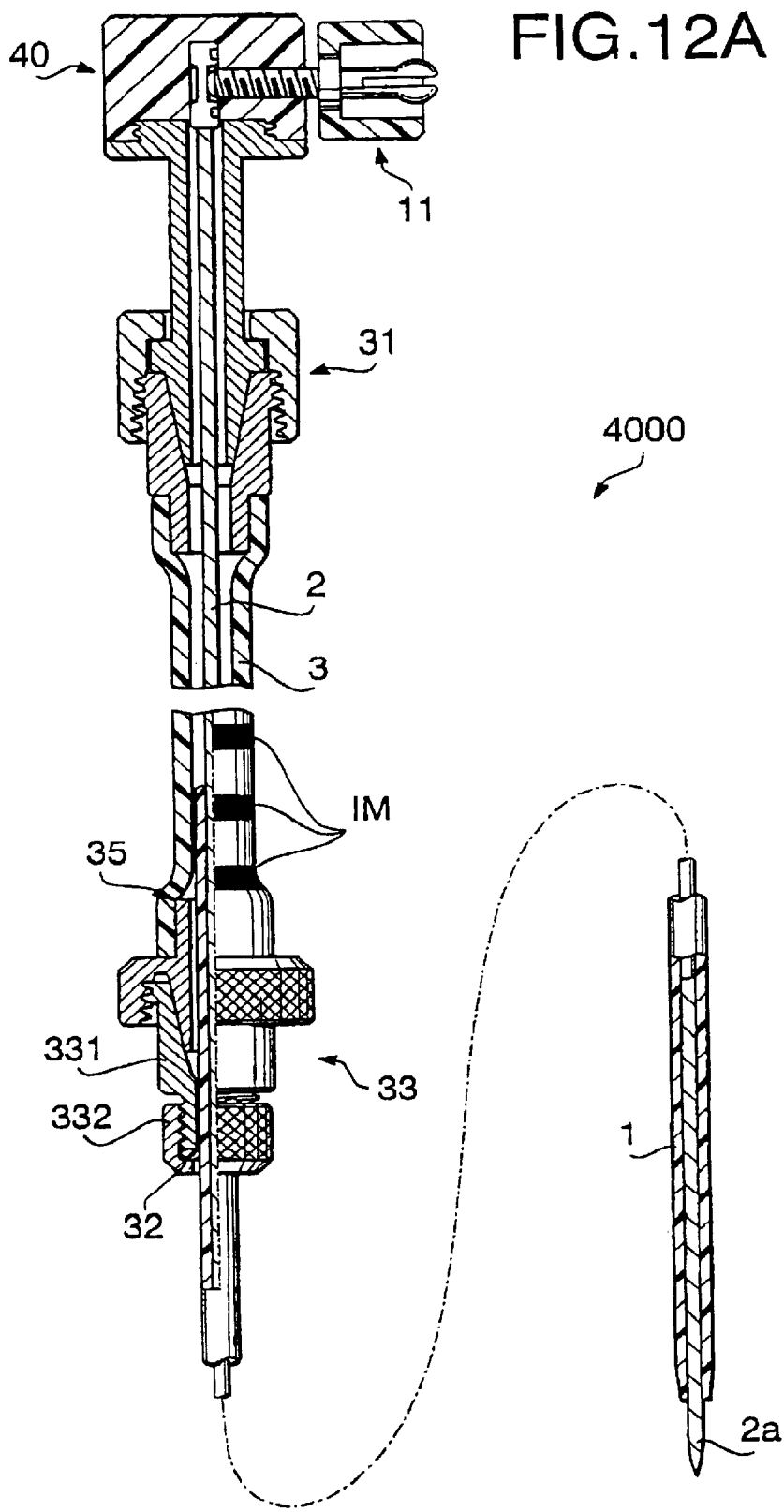
FIGS. 12A and 12B show a cross sectional views of a drainage indwelling device according to a fourth embodiment.
Figure 12B:
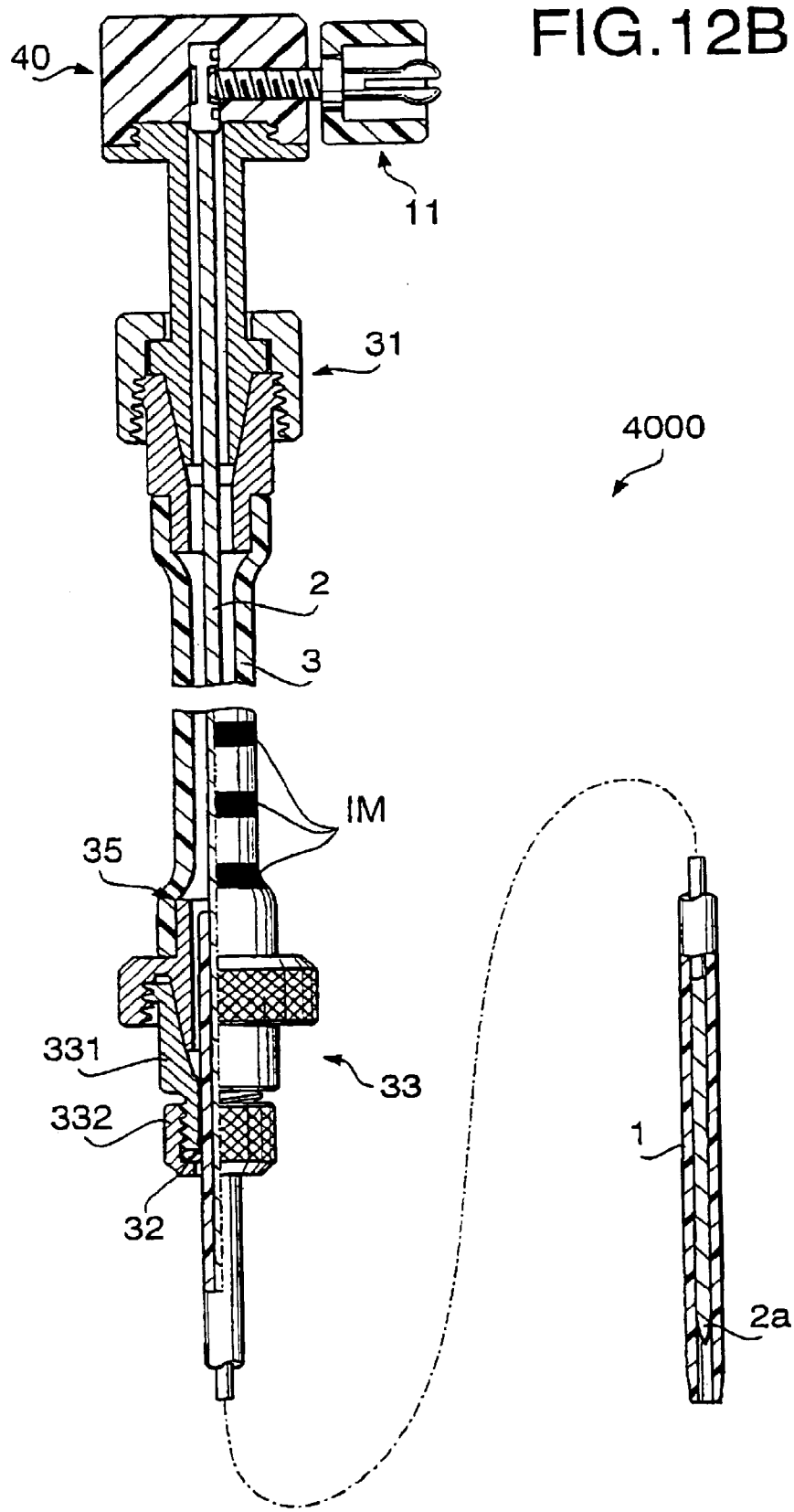

FIGS. 12A and 12B show a cross section of a drainage indwelling device 4000 according to a fourth embodiment of the invention. A reference numeral 2 denotes a guide wire. The guide wire 2 is an electrically conductive single wire or a stranded wire. The distal end portion 2a of the guide wire 2 is formed to be a needle or conical shape having a pointed tip so as to transfix the tissue. At the proximal end of the guide wire 2, a knob 40 is provided. To the knob 40, a connector 11 is provided. The connector 11 is to be connected to a high-frequency power cord (not shown). By energizing the guide wire 2 with the high-frequency current, heat is generated at the distal end portion 2a of the guide wire 2, and the inner wall of the human cavity can be transfixed. Thus, the tip portion 2a of the guide wire 2 is not necessarily pointed.

A drainage tube 1 is slidably fitted on the guide wire 2. The drainage tube 1 is made of flexible fluoro-plastic and is longer than the length of an insertion channel of an endoscope.

In other words, over the entire length of the drainage tube 1, the guide wire 2 is slidably inserted. By moving the drainage tube 1 relative to the guide wire 2 along the axis thereof at the proximal end, the tip end portion 2a of the guide wire 2 can be protruded/retracted with respect to the distal end of the drainage tube 1.

To the knob 40 secured to the proximal end of the guide wire 2, a proximal end portion of a connection tube 3 covering the proximal end portion of the guide wire 2 is detachably connected. The connection tube 3 and the guide wire 2 move integrally along the axis thereof. The connection tube 3 is connected to the knob 40 via a Luer-Lok type connection nut 11. At the distal end of the connection tube 3, an adjusting nut 33 is provided. To the adjusting nut 33, an O-ring 32 which closely contact the outer circumferential surface of the drainage tube 1 is provided. By fastening screw members 331 with respect to the screw member 332, the end surface of the screw member 331 compresses the O-ring 32 to deform and press-contact the drainage tube 1, thereby the drainage tube 1 is press secured with respect to the guide wire 2 by the O-ring 32. By loosening the engagement between the screw members 331 and 332, engagement between the drainage tube 1 and the guide wire 2 caused by the O-ring 32 is released.

The length of the connection tube 3 equals approximately a difference between the lengths of the guide wire 2 and the drainage tube 1. When the distal end portion 2a of the guide wire 2 is located at the tip end of the drainage tube 1, the proximal end of the drainage tube 1 is located at the distal end side of the connection tube 3.

Specifically, in the fourth embodiment, when the distal end portion 2a of the guide wire 2 is located exactly at the distal end of the drainage tube 1, the proximal end of the drainage tube 1 is located at a border 35 between the adjusting nut 33 and the connection tube 3.

The connection tube 3 is formed of fluoro-plastic or the like which is transparent and less elasticity. At the distal end portion thereof, a plurality of ring-shaped indication marks IM are formed at predetermined interval in the axial direction.

Thus constituted drainage indwelling device 4000 according to the fourth embodiment, when the distal end portion 2a of the guide wire 2 is protruded by a certain amount from the distal end of the drainage tube 1 as shown in FIG. 12A, the proximal end of the drainage tube 1 is inserted in the connection tube 3 by the same amount as the protruded amount.

Since the connection tube 3 is transparent, the position of the proximal end of the drainage tube 1 is observable through the connection tube 3 from outside. Accordingly, in accordance with the position of the proximal end of the drainage tube 1 with respect to the indication marks IM, the protruded amount of the distal end of the guide wire 2 with respect to the distal end of the drainage tube 1 can be recognized.

As shown in FIG. 12B, when the distal end portion 2a of the guide wire 2 is retracted inside the drainage tube 1 by a certain amount with respect to the distal end thereof, the proximal end of the drainage tube 1 is inserted in the adjusting nut 13, and is not observable from outside. In this case, i.e., when the proximal end of the drainage tube 1 cannot be observed from outside, it is recognized that the distal end portion 2a of the guide wire 2 is retracted in the drainage tube 1.

It should be noted that the indication marks IM may be formed by a user before a treatment is performed. If the indication marks IM are formed before the treatment, in accordance with the actual positional relationship between the guide wire and the drainage tube, errors due to individual extraction and contraction can be avoided.

Figure 13:
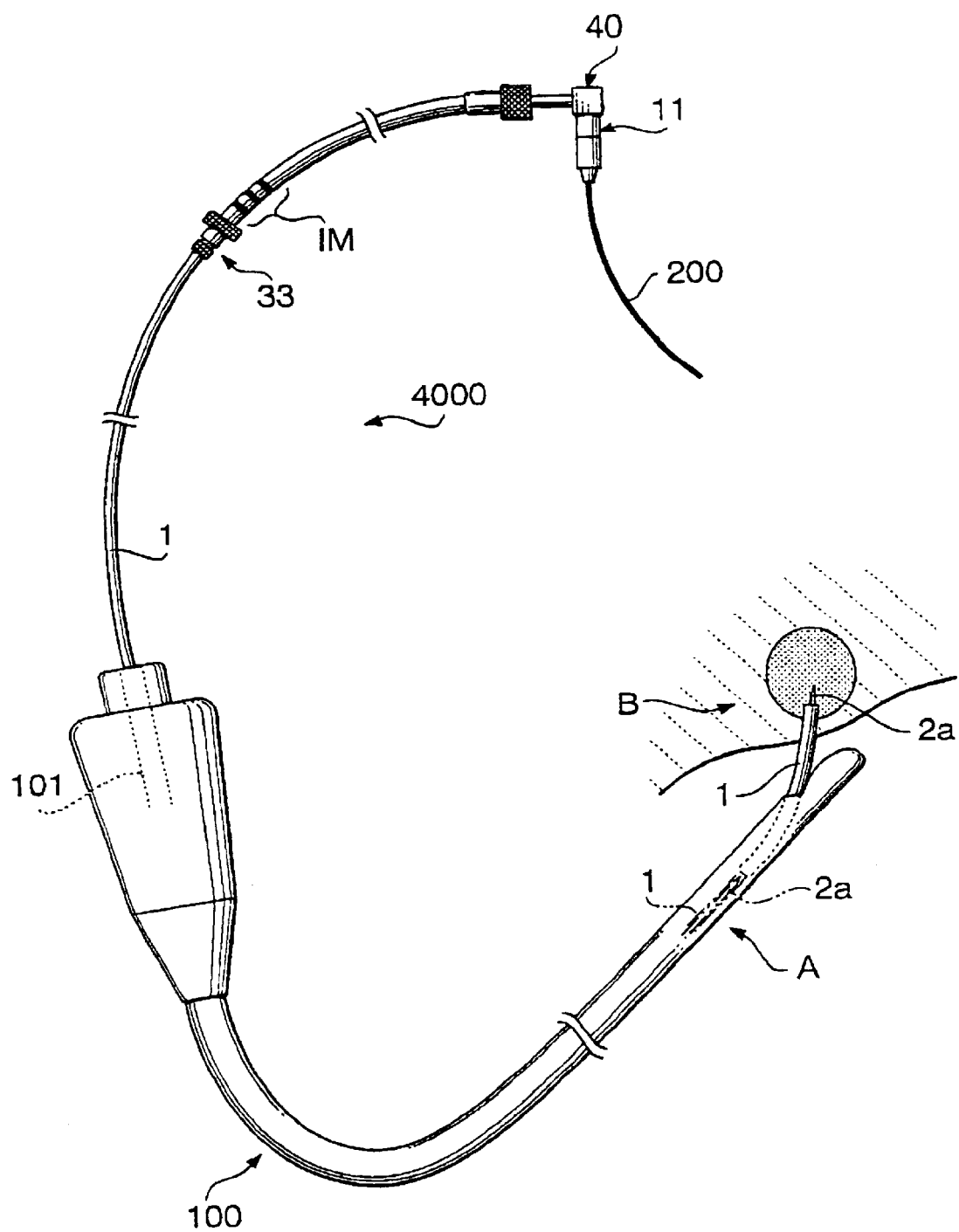
FIG. 13 shows usage of the drainage tube indwelling device according to the fourth embodiment.

FIG. 13 shows usage of the drainage tube indwelling device 4000 according to the fourth embodiment.

Firstly, the adjusting nut 33 is set such that the distal end portion 2a of the guide wire 2 is withdrawn inside the drainage tube 1, and the drainage tube 1 is fixed to onto the guide wire 2. Then, the drainage tube 1 is inserted in the insertion channel 101 of the endoscope 100. As indicated by "A", when the distal end of the drainage tube 1 is in the insertion channel 101, the drainage tube 1 remains fixed onto the guide wire 2 (i.e., the distal end portion 2a of the guide wire 2 is retracted inside the drainage tube 1). When the distal end of the drainage tube 1 is protruded from the insertion channel 101, as indicated by "B", the engagement between the guide wire 2 and the drainage tube 1 is released.

Then, by energizing the guide wire 2 with the high-frequency current, and abutting the distal end portion 2a to the inner wall of the human cavity to transfix the same. At this stage, a protruded amount of the distal end portion 2a of the guide wire 2a with respect to the distal end of the drainage tube 1 can be recognized.

When the distal end portion 2a of the guide wire 2 reaches a target position, then the drainage tube 1 is pushed using the guide wire 2 as a guide. After the distal end of the drainage tube 1 reaches the target position, the connector 11 is unscrewed to release the guide wire 2 and the connection nut 31 is loosened to remove the knob 40. Then, the endoscope 100 and the guide wire 2 are removed in this order from the proximal end side of the drainage tube 1. thus, the drainage tube 1 is indwelled.

Figure 14A:
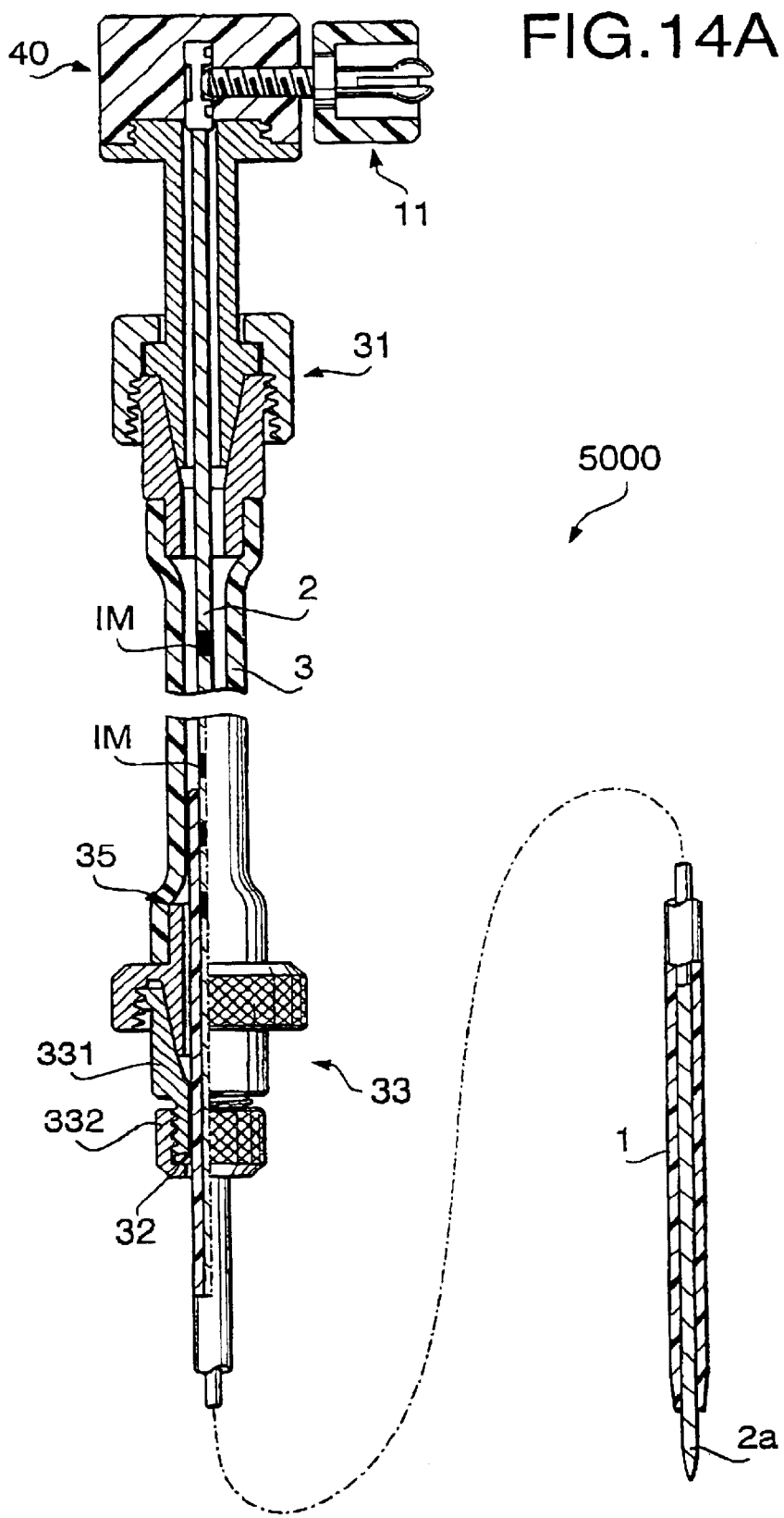
FIGS. 14A and 14B are cross sectional views of a drainage tube indwelling device according to a fifth embodiment.
Figure 14B:
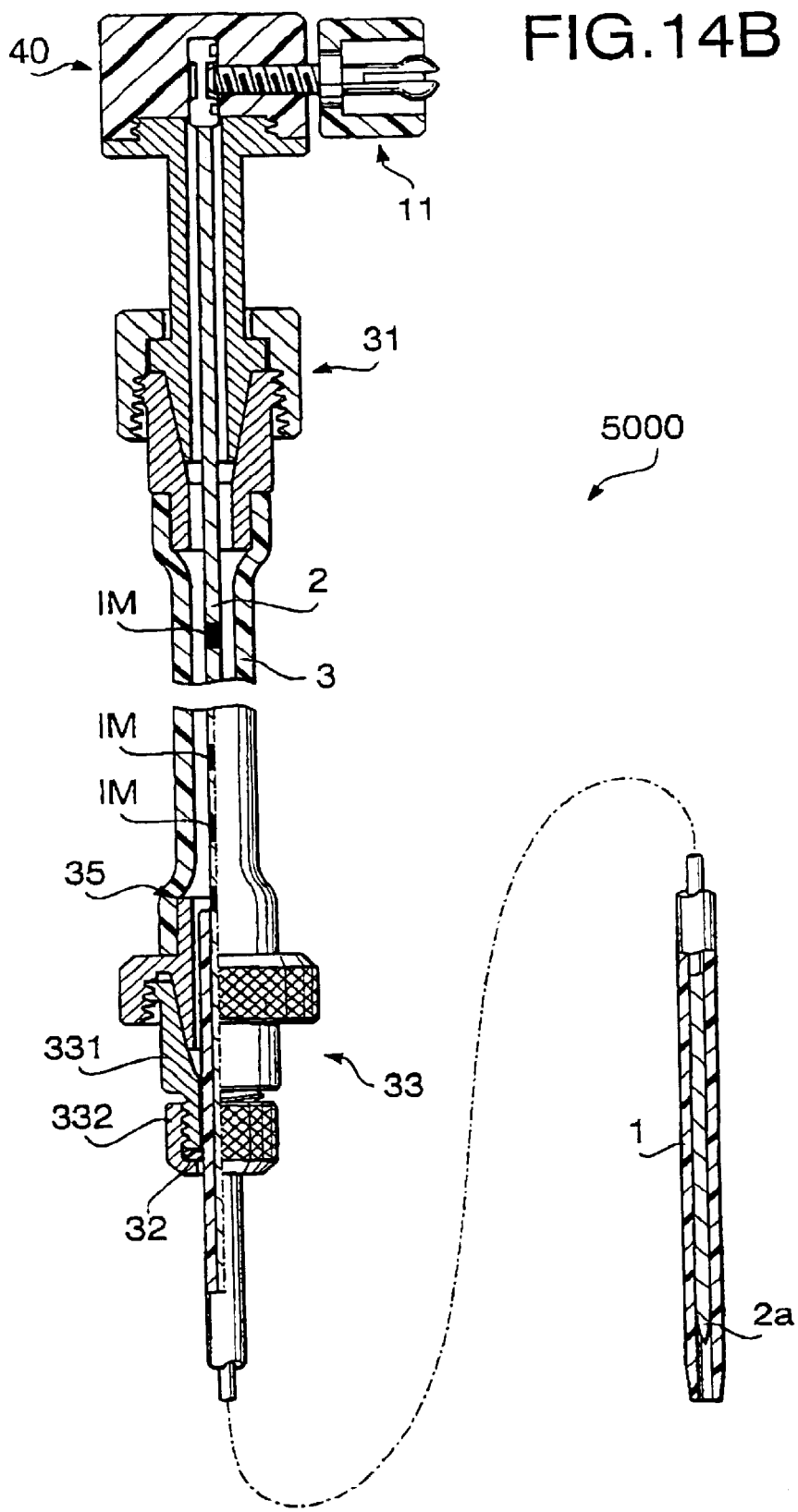

FIGS. 14A and 14B are cross sectional views of a drainage tube indwelling device 5000 according to a fifth embodiment of the invention. In FIG. 14A, a distal end portion 2a of a guide wire 2 is protruded from a drainage tube 1, while, in FIG. 14B, the distal end portion 2a of the guide wire 2 is retracted in the drainage tube 1.

The structure of the drainage tube indwelling device 5000 according to the fifth embodiment is substantially the same as the fourth embodiment, except that indication marks IM are provided on the guide wire 20. Since the indication marks IM are provided on the guide wire 20, a positional relationship between the proximal end of the drainage tube 1 and the indication marks IM can be observed through the connection tube 10 made of transparent material.

Figure 15A:
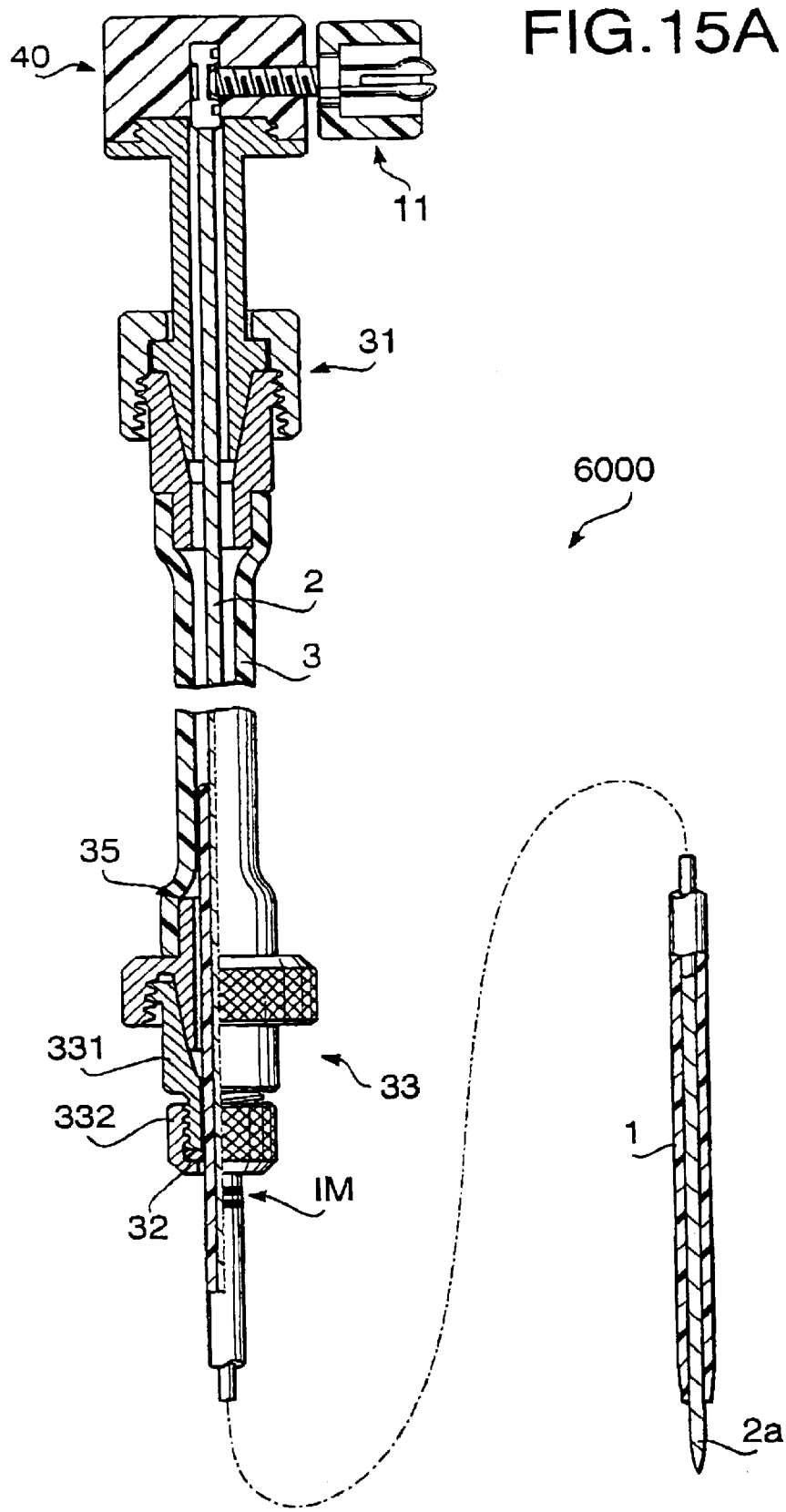
FIGS. 15A and 15B are cross sectional views of a drainage tube indwelling device according to a sixth embodiment.
Figure 15B:
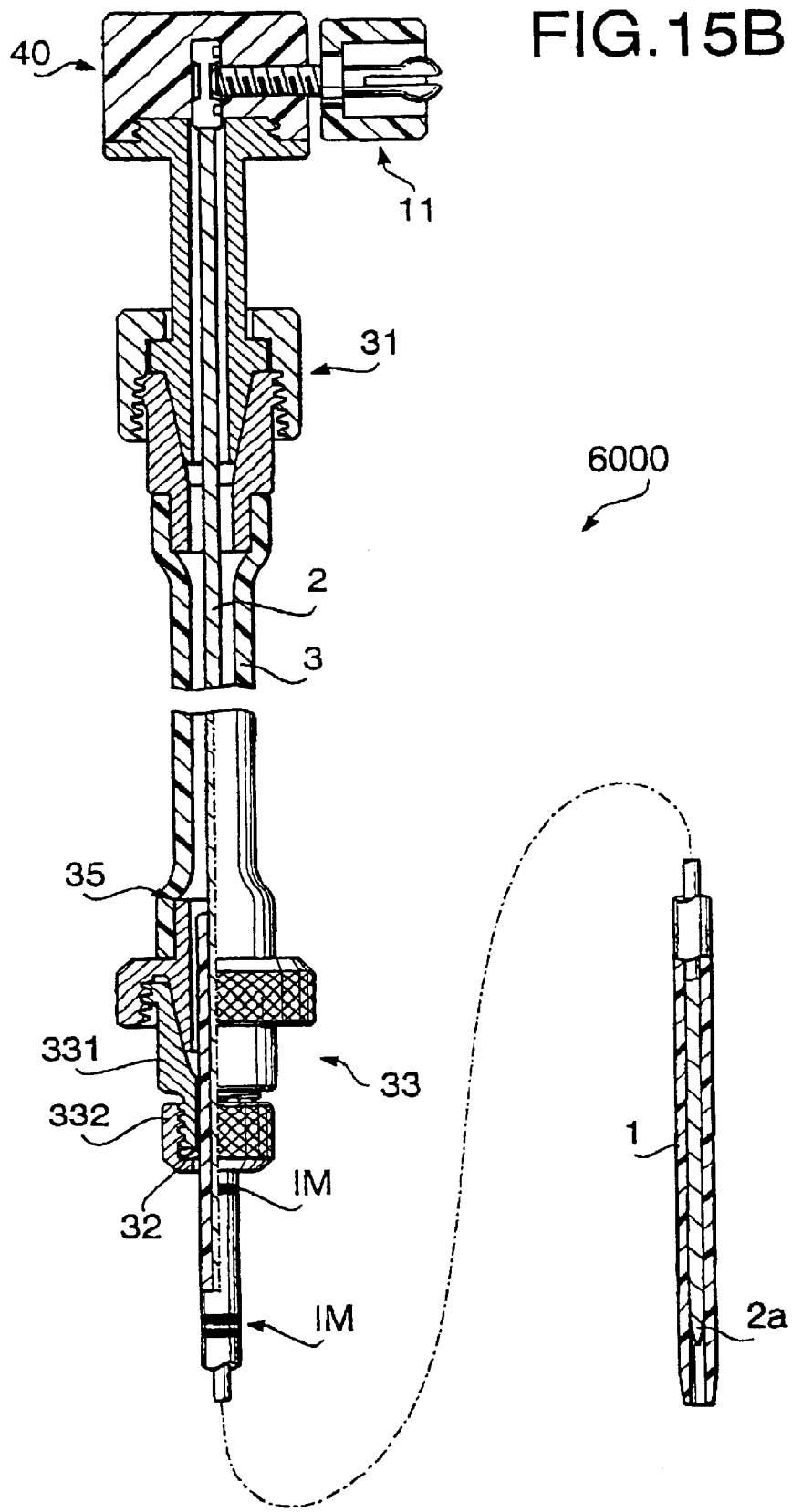

FIGS. 15A and 15B are cross sectional views of a drainage tube indwelling device 6000 according to a sixth embodiment of the invention. In FIG. 15A, a distal end portion 2a of a guide wire 2 is protruded from a drainage tube 1, while, in FIG. 15B, the distal end portion 2a of the wire 2 is retracted in the drainage tube 1.

The structure of the drainage tube indwelling device 6000 according to the sixth embodiment is substantially the same as the fourth embodiment, except that indication marks IM are provided on the outer circumferential surface of the drainage tube 1 at a position in the vicinity of the proximal end thereof. Since the indication marks IM are provided on the drainage tube 1i a positional relationship between the indication marks IM provided on the proximal end of the drainage tube 1 and the distal end side surface 26 of the adjusting nut 33 can be observed from the outside.

In accordance with a positional relationship between the distal end side surface 36 of the nut 33 and the indication mark IM, the protruded/retracted condition of the distal end portion 2a of the guide wire 2 with respect to the distal end of the drainage tube 1, and the amount thereof can be recognized.

Figure 12C:
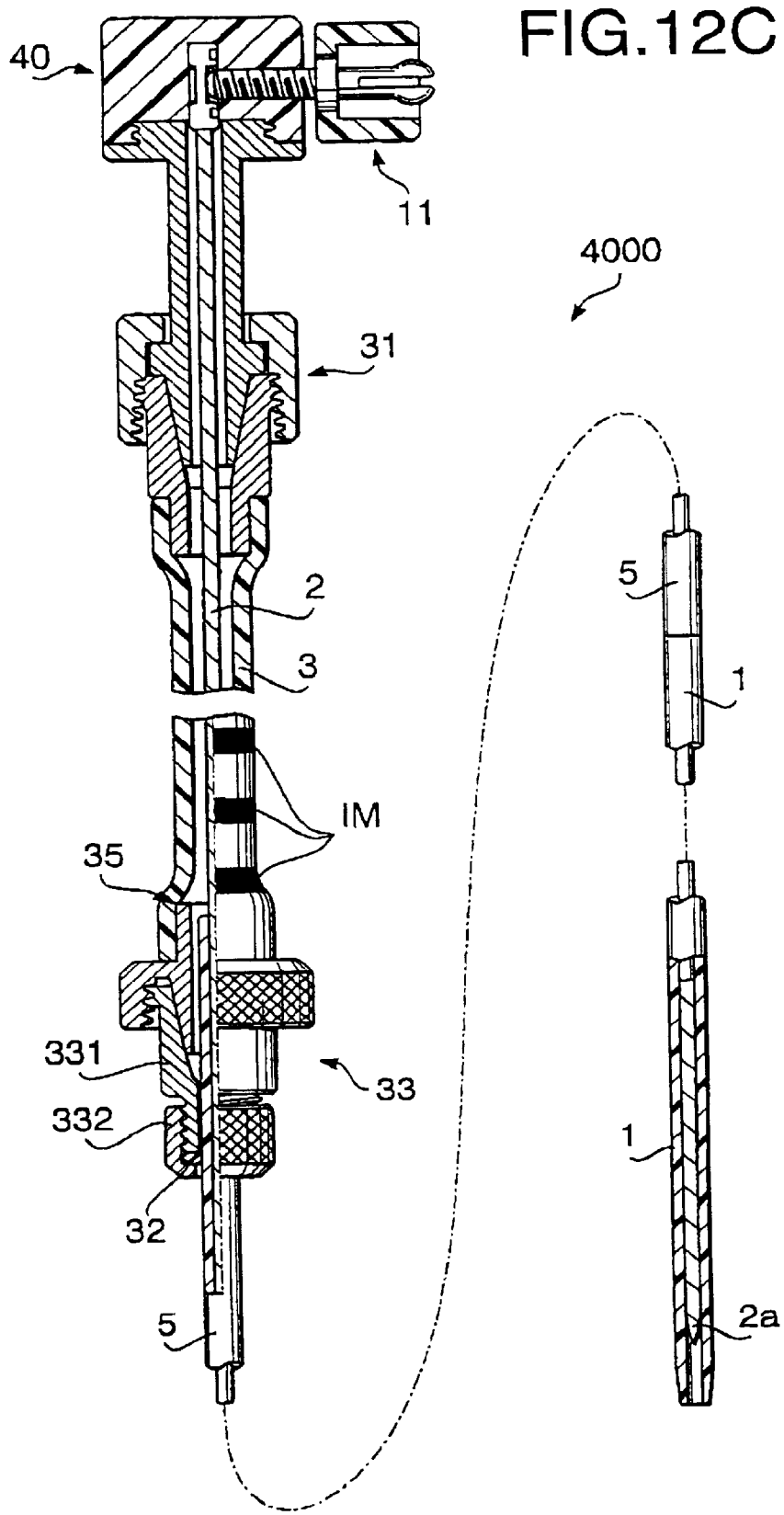
FIG. 12C shows a modification of the fourth embodiment.
Figure 14C:
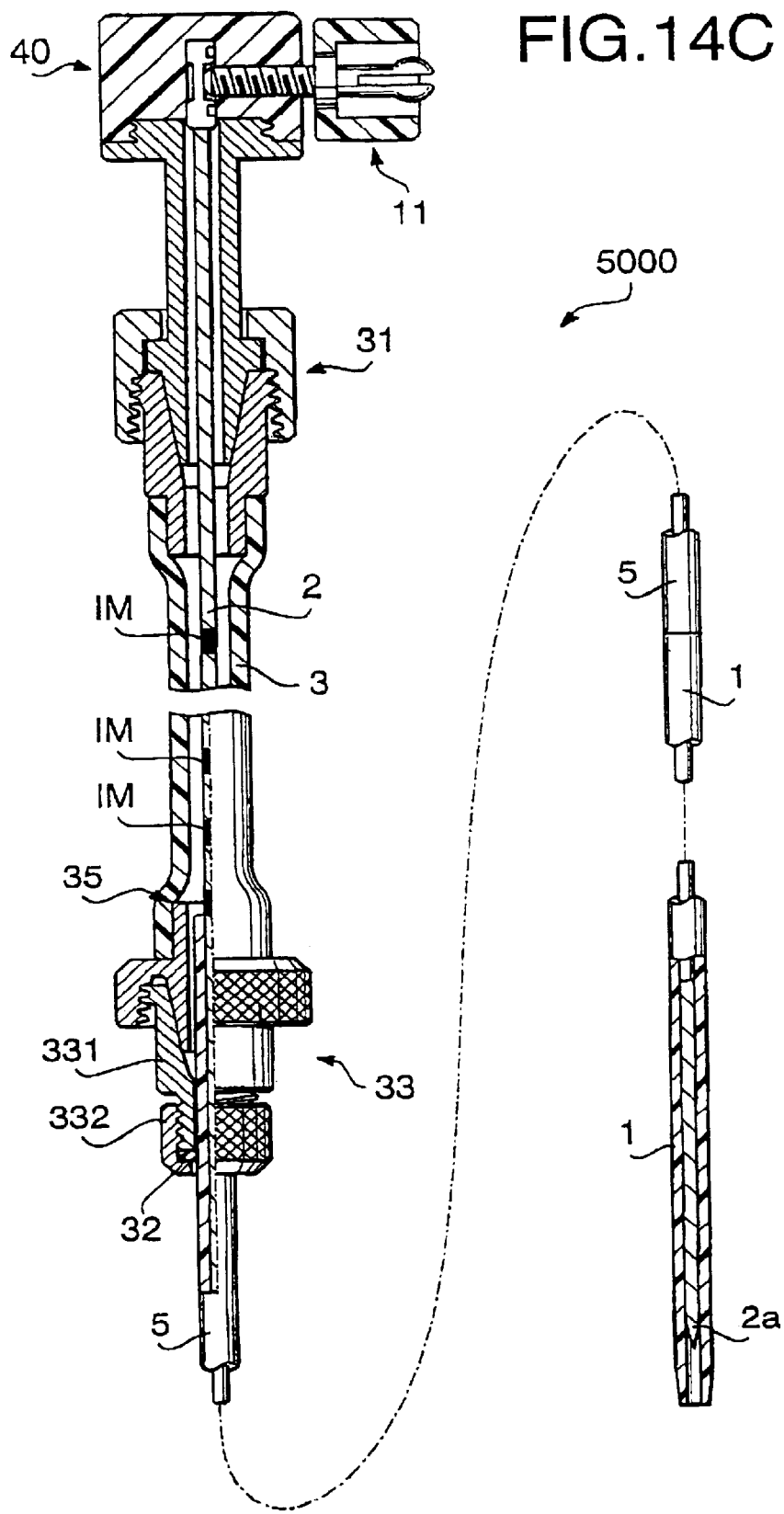
FIG. 14C shows a modification of the fifth embodiment.
Figure 15C:
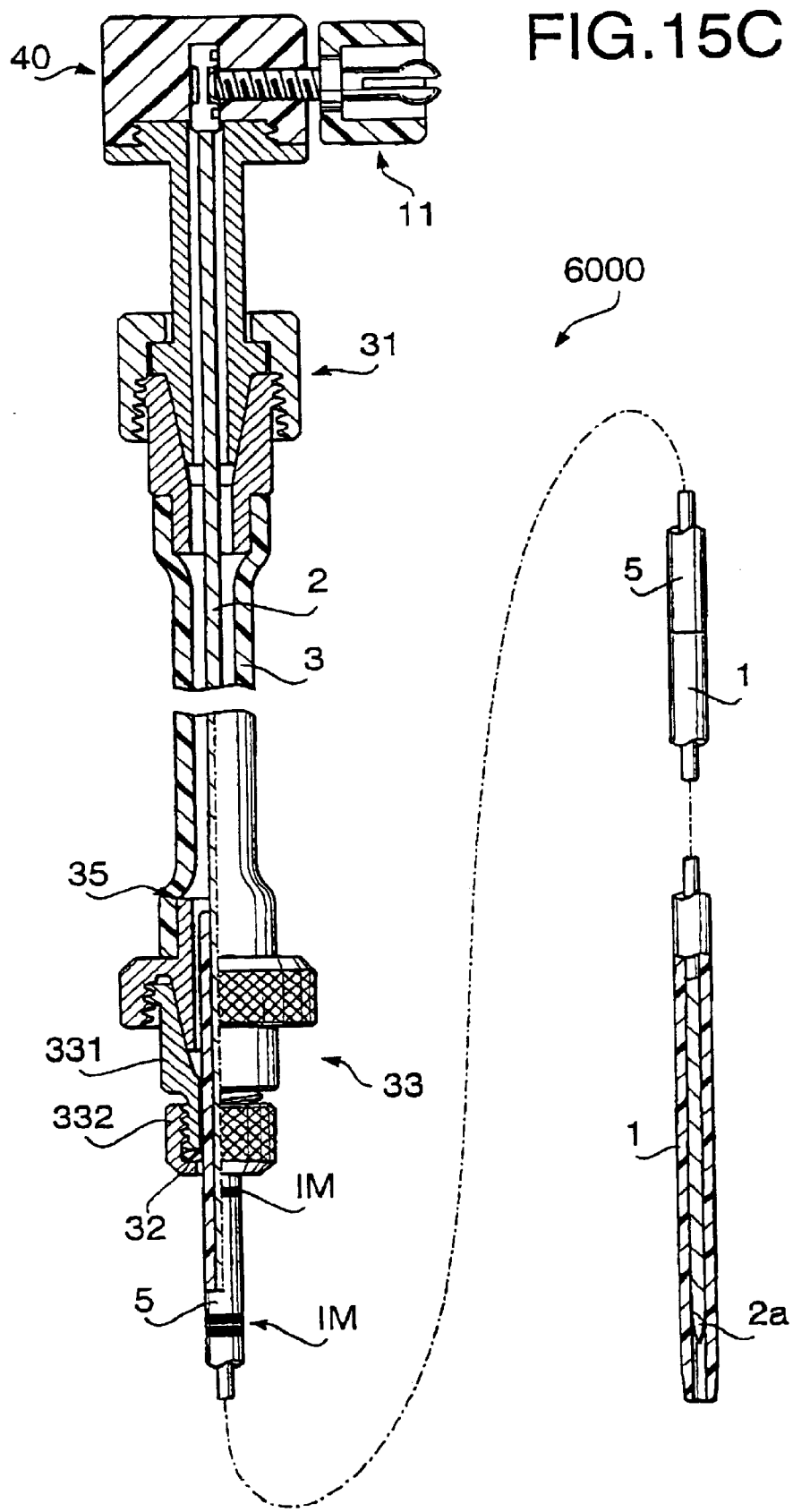
FIG. 15C shows a modification of the sixth embodiment.

The fourth to sixth embodiments may be modified to have a pusher tube for pushing the drainage tube 1 towards the distal end side thereof. FIGS. 12C, 14C and 15C respectively show such modifications. In these modifications, A pusher tube 5 is slidably fitted on the guide wire 2 and located on the proximal end side of the drainage tube 1. The pusher tube 5 is caught by the adjusting not 33, and the indication mark IM may be formed on the connection tube 10 (FIG. 12C), on the guide wire 2 (FIG. 14C), or the pusher tube 5 (FIG. 15C).

According to the fourth to sixth embodiments and modifications thereof, since the protruded amount of the distal end portion 2a of the guide wire 2 is adjusted using the nut 33, and the protruded/retracted amount of the distal end portion 2a can be recognized with reference to the indication marks IM. Therefore, when the drainage tube indwelling device is inserted in a treatment accessory insertion channel of the endoscope, retraction of the end portion 2a of the guide wire 2 can be confirmed, and the insertion channel may not be damaged by the tip of the end portion 2a even if it is sharpened.

It should be noted that the marks IM may have various colors, length (in the axial direction), textures or patterns to indicate various positions.

The present disclosure relates to the subject matters contained in Japanese Patent Applications No. HEI 10-254256, filed on Sep. 8, 1999, and HEI 11-047282, filed on Feb. 25, 1999, which are expressly incorporated herein by reference in their entireties.

What is claimed is:

1. A drainage tube indwelling device for an endoscope, comprising:

a drainage tube formed of an electrically insulating flexible material, said drainage tube being longer than a length of a treatment insertion channel of the endoscope, said drainage tube adapted to be slidably inserted in the treatment insertion channel;

a guide wire formed of an electrically conductive material, said guide wire being longer than said drainage tube, said guide wire being slidably inserted in said drainage tube, a distal end portion of said guide wire protruding from a distal end of said drainage tube;

a connector that connects said guide wire with a high-frequency power source;

a fixing device capable of releasably fixing a position of said drainage tube with respect to said guide wire; and an operation unit for moving said device in an axial direction of said drainage tube, said operation unit including a stationary unit to be secured at an inlet of the insertion channel of the endoscope, and a slider unit which is slidable with respect to said stationary unit, and wherein said slider unit moves said fixing device.

2. The drainage tube indwelling device according to claim 1, wherein said connector and said fixing device are integrally formed and provided at a proximal end of said drainage tube.

3. The drainage tube indwelling device according to claim 1, further comprising an electrically insulating flexible tube provided between the proximal end portion of said drainage tube and a proximal end of said guide wire, said flexible tube preventing a portion of said guide wire located between the proximal end of said drainage tube and the proximal end of said guide wire from being exposed to outside.

4. The drainage tube indwelling device according to claim 3, wherein said fixing device is capable of fixing said drainage tube, said guide wire and said flexible tube with each other.

5. The drainage tube indwelling device according to claim 1, wherein said fixing device is capable of fixing said drainage tube and said guide wire with each other.

6. The drainage tube indwelling device according to claim 1, further comprising an indicating system for indicating a positional relationship between said drainage tube and said guide wire in an axial direction thereof.

7. The drainage tube indwelling device for an endoscope according to claim 1, said fixing device comprising a force applying device that applies a releasable force external of said drainage tube and said guide wire.

8. The drainage tube indwelling device for an endoscope according to claim 1, said fixing device being positioned adjacent a proximal end and externally of said drainage tube.

9. The drainage tube indwelling device for an endoscope according to claim 1, said fixing device releasably fixing said drainage tube with respect to said guide wire at any of a plurality of positions.

10. A drainage tube indwelling device for an endoscope, comprising:
   a drainage tube;
   a guide wire insertable in said drainage tube, said drainage tube adapted to be inserted in an accessory insertion channel of the endoscope with said guide wire inserted;
   an adjustment member that adjusts a positional relationship between said drainage tube and said guide wire in an axial direction;
   a indicating system that indicates a positional relationship between sad drainage tube and said guide wire in the axial direction; and
   a transparent tube member provided on a proximal end side of said adjustment member, said transparent tube member covering a proximal end portion of said drainage tube, a positional relationship between said drainage tube and said guide wire being observable through said transparent tube member.

11. The drainage tube indwelling device according to claim 10, wherein said indicating system includes an indication mark provided on said guide wire.

12. The drainage tube indwelling device according to claim 10, wherein said indicating system includes an indication mark provided on said transparent tube.

13. The drainage tube indwelling device for an endoscope according to claim 10, said adjustment member comprising a resilient member positioned about said drainage tube and a force applying member configured to apply a force against and compress the resilient member to secure said drainage tube with respect to said guide wire.

14. The drainage tube indwelling device for an endoscope according to claim 10, said adjustment member being positioned adjacent a proximal end and externally of said drainage tube.

15. A drainage tube indwelling device for an endoscope, comprising:
   a drainage tube;
   a guide wire insertable in said drainage tube, said drainage tube adapted to be inserted in an accessory insertion channel of the endoscope with said guide wire inserted;
   an adjustment member that adjusts a positional relationship between said drainage tube and said guide wire in an axial direction;
   an indicating system that indicates a positional relationship between said drainage tube and said guide wire in the axial direction; and
   a pusher tube located on a proximal end side of said drainage tube, said pusher tube beg slidably fitted on said guide wire, the distal end of said pusher tube contacting the proximal end of said drainage tube.

16. The drainage tube indwelling device according to claim 15, wherein said indicating system includes an indication mark provided on said drainage tube, said indication mark indicates a positional relationship between said drainage tube and said adjustment member.

17. The drainage tube indwelling device according to claim 15, wherein said indicating system includes an indication mark provided on said guide wire.

18. The drainage tube indwelling device according to claim 15, wherein said indicating system includes an indication mark provided on said pusher tube, said indication mark indicates a positional relationship between said pusher tube and said adjustment member.

19. The drainage tube indwelling device according to claim 15, further comprising a transparent tube member provided on a proximal end side of said adjusting mechanism, said transparent tube member covering a proximal end portion of said pusher tube, a positional relationship between said pusher tube and said guide wire being observable through said transparent tube member, a positional relationship between said drainage tube and said guide wire corresponding to the positional relationship between said drainage tube and said guide wire.

20. The drainage tube indwelling device according to claim 15, wherein said indicating system includes an indication mark provided on said transparent tube.

* * * * *